(12) United States Patent
Sakon et al.

(10) Patent No.: US 8,450,273 B2
(45) Date of Patent: May 28, 2013

(54) FUSION PROTEINS OF COLLAGEN-BINDING DOMAIN AND PARATHYROID HORMONE

(75) Inventors: Joshua Sakon, Fayetteville, AR (US); Robert C. Gensure, Luling, LA (US); Osamu Matsushita, Kanagawa (JP)

(73) Assignees: The Board of Trustees of the University of Arkansas, Little Rock, AR (US); Ochsner Clinic Foundation, New Orleans, LA (US); National University Corporation Kagawa University, Takamatsu-shi, Kagawa (JP)

( * ) Notice: Subject to any disclaimer, the term of this patent is extended or adjusted under 35 U.S.C. 154(b) by 670 days.

(21) Appl. No.: 12/594,547

(22) PCT Filed: Apr. 9, 2008

(86) PCT No.: PCT/US2008/004589
§ 371 (c)(1),
(2), (4) Date: Oct. 2, 2009

(87) PCT Pub. No.: WO2008/124166
PCT Pub. Date: Oct. 16, 2008

(65) Prior Publication Data
US 2010/0129341 A1 May 27, 2010

Related U.S. Application Data

(60) Provisional application No. 60/922,433, filed on Apr. 9, 2007.

(51) Int. Cl.
*A61K 38/10* (2006.01)
*A61K 38/16* (2006.01)
*A61K 39/00* (2006.01)
*A61K 38/39* (2006.01)
*C07K 14/635* (2006.01)

(52) U.S. Cl.
USPC ....... 514/11.8; 514/17.2; 514/21.2; 514/21.3; 514/21.5; 530/324; 530/326; 530/327; 424/185.1; 424/192.1

(58) Field of Classification Search
None
See application file for complete search history.

(56) References Cited

U.S. PATENT DOCUMENTS

| | | | |
|---|---|---|---|
| 6,362,163 | B1 | 3/2002 | Gardella et al. |
| 2002/0102709 | A1* | 8/2002 | Ishikawa et al. ............... 435/226 |
| 2002/0164719 | A1 | 11/2002 | Hall et al. |
| 2003/0187232 | A1 | 10/2003 | Hubbell et al. |
| 2004/0053368 | A1 | 3/2004 | Ishikawa et al. |
| 2005/0119183 | A1* | 6/2005 | Wells et al. ................... 514/12 |
| 2005/0180986 | A1 | 8/2005 | Rich et al. |
| 2006/0014687 | A1 | 1/2006 | Crine et al. |
| 2006/0257376 | A1 | 11/2006 | Scadden et al. |

FOREIGN PATENT DOCUMENTS

| | | |
|---|---|---|
| EP | 0207751 | 1/1987 |
| EP | 1314780 | 5/2003 |
| EP | 1557176 | 7/2005 |
| WO | WO 00/06195 | 2/2000 |
| WO | WO 00/49159 | 8/2000 |
| WO | WO 03/052091 | 6/2003 |
| WO | WO 2004/071543 | 8/2004 |
| WO | WO 2006/072623 | 7/2006 |

OTHER PUBLICATIONS

Yoshihara, 1994, J. Bacteriology, 176, 6489-6496.*
Nishi, 1998, PNAS, 95, 7018-7023.*
Seeman, E. et al., "Reconstructing the skeleton with intermittent parathyroid hormone," Trends Endocrinol Metab. (2001) 12(7):281-3.
Shen, V. et al., "Skeletal effects of parathyroid hormone infusion in ovariectomized rats with or without estrogen repletion, " J Bone Miner Res. (2000) 15(4):740-6.
Shinoda, Y. et al., "Mechanisms underlying catabolic and anabolic functions of parathyroid hormone on bone by combination of culture systems of mouse cells, " J. of Cellular Biology (2010) 109(4):755:63.
Silver, J. et al., "Harnessing the parathyroids to create stronger bones," Curr Opin Nephrol Hypertens. (2004) 13(4):471-6.
Silverberg, S.J. et al., "Skeletal disease in primary hyperparathyroidism," J Bone Miner Res., (1989) 4(3):283-91.
Skripitz, R. et al., "Parathyroid hormone—a drug for orthopedic surgery?," Acta Orthop Scand. (2004) 75(6):654-62.
Skripitz, R. et al., "Stimulation of implant fixation by parathyroid hormone (1-34)—A histomorphometric comparison of PMMA cement and stainless steel," J Orthop Res. (2005) 23(6):1266-70. Epub Jun. 16, 2005
Smajilovic, S. et al., "Effect of intermittent versus continuous parathyroid hormone in the cardiovascular system of rats, " Open Cardiovasc. Med. J. (2010) 4:110-6.
Spurney, R.F. et al., "Anabolic effects of a G protein-coupled receptor kinase inhibitor expressed in osteoblasts," J Clin Invest. (2002) 109(10):1361-71.
Stracke, S. et al., "Long-term outcome after total parathyroidectomy for the management of secondary hyperparathyroidism, " Nephron Clin Pract. (2009) 111(2):c102-9. Epub Jan. 13, 2009.
Strewler, G.J., "Local and systemic control of the osteoblast," J. of Clin. Invest. (2001) 107:271-272.

(Continued)

Primary Examiner — Satyanarayana R Gudibande
(74) Attorney, Agent, or Firm — Andrus, Sceales, Starke & Sawall, LLP

(57) ABSTRACT

Fusion proteins containing active agonist or antagonist fragments of parathyroid hormone (PTH) and parathyroid hormone related peptide (PTHrP) coupled to a collagen-binding domain are presented. The fusion proteins can be used to promote bone growth, to promote hair growth, to prevent cancer metastasis to bone, to promote immune reconstitution with a bone marrow stem cell transplant, to promote mobilization of bone marrow stem cells for collection for autologous stem cell transplant, and to treat renal osteodystrophy. Pharmaceutical agents comprising a collagen-binding polypeptide segment linked to a non-peptidyl PTH/PTHrP receptor agonist or antagonist are also presented.

7 Claims, 7 Drawing Sheets

OTHER PUBLICATIONS

Suttamanatwong, S. et al., "Regulation of matrix Gla protein by parathyroid hormone in MC3T3-3-E1 osteoblast-like cells involves protein kinase A and extracellular signal-regulated kinase pathways," J Cell Biochem. (2007) 102(2):496-505.

Suttamanatwong, S. et al, "Sp proteins and Runx2 mediate regulation of matrix gla protein (MGP) expression by parathyroid hormone," J Cell Biochem. (2009) 107(2):284-92.

Suzuki, A. et al., "PTH/cAMP/PKA signaling facilitates canonical Wnt signaling via inactivation of glycogen synthase kinase-3beta in osteoblastie Saos-2 cells," J Cell Biochem. (2008) 104(1):304-17.

Swarthout, J.T. et al., "Parathyroid hormone-dependent signaling pathways regulating genes in bone cells," Gene (2002) 282(1-2):1-17.

Swarthout, J.T. et al., "Stimulation of extracellular signal-regulated kinases and proliferation in rat osteoblastic cells by parathyroid hormone is protein kinase C-dependent," J Biol Chem. (2001) 276(10):7586-92. Epub Dec. 6, 2000.

Takada, H. et al., "Response of parathyroid hormone to anaerobic exercise in adolescent female athletes, " Acta Paediatr Jpn. (1998) 40(1):73-7.

Takasu, H. et al., "Dual signaling and ligand selectivity of the human PTH/PTHrP receptor, " J Bone Miner Res. (1999) 14(1):11-20.

Talmage, R.V. et al., "Calcium homeostasis: reassessment of the actions of parathyroid hormone," Gen Comp Endocrinol. (2008) 156(1):1-8. Epub Nov 12, 2007.

Tam, C.S. et al., "Parathyroid hormone stimulates the bone apposition rate independently of its resorptive action: differential effects of intermittent and continuous administration," Endocrinology (1982) 110(2):506-12.

Tawfeek, H. et al., "Disruption of PTH receptor 1 in T cells protects against PTH-induced bone loss," PLoS (2010) 5(8):e12290.

Tokumoto, M. et al., "Parathyroid cell growth in patients with advanced secondary hyperparathyroidism: vitamin D receptor, calcium sensing receptor, and cell cycle regulating factors," Ther Apher Dial. (2005) 9(Suppl 1):S27-34.

Tollin, S.R. et al., "Serial changes in bone mineral density and bone turnover after correction of secondary hyperparathyroidism in a patient with pseudohypoparathyroidism type Ib, " J Bone Miner Res. (2000) 15(7):1412-6.

Toyoshima, T. et al., "Collagen-binding domain of a *Clostridium histolyticum* collagenase exhibits a broad substrate spectrum both in vitro and in vivo," Connective Tissue Research (2001) 42(4):281-290.

Uzawa, T. et al., "Comparison of the effects of intermittent and continuous administration of human parathyroid hormone(1-34) on rat bone," Bone(1995) 16(4):477-84.

Vanstone, M.B. et al., "Rapid correction of bone mass after parathyroidectomy in an adolescent with primary hyperparathyroidism," J. Clin. Endocrinol. Metab. (2011) 96(2):E347-50. Epub Nov. 24, 2010.

Wan, Q. et al., "Intra-articular injection of parathyroid hormone in the temporomandibular joint as a novel therapy for mandibular asymmetry, " Med Hypotheses (2009) 74(4):685-7.

Wang, C.A. et al., "Natural history of parathyroid carcinoma. Diagnosis, treatment, and results, " Am J Surg. (1985) 149(4):522-7.

Wang, Y. et al., "A theoretical model for simulating effect of parathyroid hormone on bone metabolism at cellular level," Mol Cell Biomech. (2009) 6(2):101-12.

Wang, Y. et al., "Gender differences in the response of CD-1 mouse bone to parathyroid hormone: potential role of IGF-I," J Endocrinol. (2006) 189(2):279-87.

Watson, P.H. et al., "Enhanced osteoblast development after continuous infusion of hPTH(1-84) in the rat," Bone (1999) 24(2):89-94.

Weir, E.C. et al., "Synthetic parathyroid hormone-like protein (1-74) is anabolic for bone in vivo," Calcif Tissue Int. (1992) 51(1):30-4.

Whitfield, J.F., "Taming Psoriatic Keratinocytes-PTHs'uses go up another notch," J. Cell. Biochem. (2004) 93:251-256.

Wilson, J.J. et al., "A bacterial collagen-binding domain with novel calcium-binding motif controls domain orientation," EMBO Journal (2003) 22(8)1743-1752.

Xu, M. et al., "Basal bone phenotype and increased anabolic responses to intermittent parathyroid hormone in healthy male COX-2 knockout mice," Bone (2010) 47(2):341-52. Epub May 13, 2010.

Yang, C, et al., "Effects of continuous and pulsatile PTH treatments on rat bone marrow stromal cells," Biochem Biophys Res Commun. (2009) 380(4);791-6. Epub Feb 3, 2009.

Yoshihara, K. et al., "Cloning and nucleotide sequence analysis of the coIH gene from *Clostridium histolyticum* encoding a collagenase and a gelatinase," J Bacteriol (1994) 176:6489-6496.

Younes, N. A. et al., "Laboratory screening for hyperparathyroidism," Clin Chim Acta. (2005) 353(1-2):1-12.

Zang, X.Y. et al., "Effects of parathyroid hormone and estradiol on proliferation and function of human osteoblasts from fetal long bone: An in vitro study," Chin Med J (Engl). (1994) 107(8):600-3.

Zaruba, M.M. et al., "Parathyroid hormone treatment after myocardial infarction promotes cardiac repair by enhanced neovascularization and cell survival, " Cardiovasc Res (2008) 77(4):722-731.

International Search Report and Written Opinion of the International Searching Authority for Application No. PCT/US08/004589 dated Oct. 28. 2008 (17 pages).

European Patent Office Search Report for Application No. 08742686.2 dated Aug. 4, 2010 (8 pages).

Carter, P.H. et al., "Selective and nonselective inverse agonists for constitutively active type-1 parathyroid hormone receptors: evidence for altered receptor conformations," Endocrinology (2001) 142(4):1534-1545.

Compston, J.E., "Skeletal actions of intermittent parathyroid hormone: effects on bone remodelling and structure, " Bone (2007) 40(6):1447-1452.

Fox, J. et al., "Effects of daily treatment with parathyroid hormone 1-84 for 16 months on density, architecture and biomechanical properties of cortical bone in adult ovariectomized rhesus monkeys," Bone (2007) 41(3):321-330.

Fukayama, S. et al., "New insights into interactions between the human PTH/PTHrP receptor and agonist/antagonist binding," Am. J. Physiol. Endocrinol Metab. (1998) 274:297-303.

Gardella, T.J. et al., "Converting parathyroid hormone-related peptide (PTHrP) into a potent PTH-2 receptor agonist," J of Biological Chem (1996) 271(33):19888-19838.

Iida-Klein, A. et al., "Short-term continuous infusion of human parathyroid hormone 1-34 fragment is catabolic with decreased trabecular connectivity density accompanied by hypercalcemia in C57BL/J6 mice," J Endocrinol. (2005) 186(3):549-57.

Ishikawa, T. et al., "Production of a biologically active epidermal growth factor fusion protein with high collagen affinity," J. Biochem. (2001) 129(4)627-633.

Ito, M., "Parathyroid hormone and bone quality," Clin Calcium. (2005) 15(12):31-7.

Kido, S. et al., "Mechanism of PTH actions on bone," Clin Calcium. (2003) 13(1):14-8.

Li, X. et al., "In vivo parathyroid hormone treatments and RNA isolation and analysis," Methods Mol Biol. (2008) 455:79-87.

Locus BAA06251 (GI 710023), Collagenase precursor from *Clostridium histolyticum*, Jan. 30, 2003. This amino acid sequence is disclosed in this application as SEQ ID No. 6. The sequence of residues 901-1021 of BAA06251 corresponds to the collagen binding domain included in the fusion protein of SEQ ID No. 1.

Locus EAW68494 (GI 119588900), Parathyroid hormone isoform from Homo sapiens, Dec. 18, 2006. Residues 64-147 of EAW68494 correspond to the PTH of SEQ ID No. 7.

Rosen, C.J., "The cellular and clinical parameters of anabolic therapy for osteoporosis," Crit Rev Eukaryot Gene Expr. (2003) 13(1):25-38.

Stewart, A.F., "PTHrP(1-36) as a skeletal anabolic agent for the treatment of osteoporosis," Bone (1996) 19(4):303-306.

Zhou, H. et al., "Anabolic action of parathyroid hormone on cortical and cancellous bone differs between axial and appendicular skeletal sites in mice," Bone (2003) 32(5):513-520.

Chen, Q. et al., "Effects of an excess and a deficiency of endogenous parathyroid hormone on volumetric bone mineral density and bone geometry determined by peripheral quantitative computed tomography in female subjects," J Cin Endocrinol Metab. (2003) 88(10):4655-8.

Cherian, P.P. et al., "Role of gap junction, hemichannels, and connexin 43 in mineralizing in response to intermittent and continuous application of parathyroid hormone," Cell Commun Adhes. (2008) 15(1):43-54.

Chevalley, T. et al., "Bone and hormones. Effects of parathyroid hormone on the bone," Presse Med. (1999) 28(10):547-53.

Cohen, A. et al., "Osteoporosis in adult survivors of adolescent cardiac transplantation may be related to hyperparathyroidism, mild renal insufficiency, and increased bone turnover," J Heart Lung Transplant.(2005) 24(6):696-702.

Cormier, C., "Parathyroid hormone in osteoporosis," Presse Med. (2006) 35(3 Pt 2):495-501.

Corsi, A. et al., "Osteomalacic and hyperparathyroid changes in fibrous dysplasia of bone: core biopsy studies and clinical correlations," J Bone Miner Res. (2003) I8(7):1235-46.

Cosman, F., "Parathyroid hormone treatment for osteoporosis," Current Opinion in Endocrinology, Diabetes & Obesity (2008) 15:495-501.

Cundy, T. et al., "Hyperparathyroid bone disease in chronic renal failure," Ulster Med J. (1985) 54(Suppl):S34-43.

Datta, N. S. et al., "Distinct roles for mitogen-activated protein kinase phosphatase-1 (MKP-1) and ERK-MAPK in PTH1R signaling during osteoblast proliferation and differentiation," Cell (2010) 22(3):457-66. Epub.

Deal, C., "The use of intermittent human parathyroid hormone as a treatment for osteoporosis," Curr Rheumatol Rep. (2004) 6(1):49-58.

Demiralp, B. et al., "Anabolic actions of parathyroid hormone during bone growth are dependent on c-fos," Endocrinology (2002) 143(10):4038-47.

Dobnig, H. et al., "The effects of programmed administration of human parathyroid hormone fragment (1-34) on bone histomorphometry and serum chemistry in rats," Endocrinology(1997) 138(11):4607-12.

Drake, M.T. et al., "Parathyroid hormone increases the expression of receptors for epidermal growth factor in UMR 106-01 cells," Endocrinology (1994) 134(4):1733-7.

Endo, K. et al., "1,25-dihydroxyvitamin D3 as well as its analogue OCT lower blood calcium through inhibition of bone resorption in hypercalcemic rats with continuous parathyroid hormone-related peptide infusion," J Bone Miner Res. (2000) 15(1):175-81.

Etoh, M. et al., "Repetition of continuous PTH treatments followed by periodic withdrawals exerts anabolic effects on rat bone," J Bone Miner Metab. (2010) 28(6):641-649.

Fitzpatrick, L.A. et al., "Acute primary hyperparathyroidism," Am J Med. (1987) 82(2):275-82.

Fleming, A. et al., "High-throughput in vivo screening for bone anabolic compounds with zebrafish," J Biomol Screen. (2005) 10(8):823-31. Epub Oct. 18, 2005.

Fouda, M.A., "Primary hyperparathyroidism: King Khalid University Hospital Experience," Ann Saudi Med. (1999) 19(2):110-5.

Fraher, L.J. et al., "Comparison of the biochemical responses to human parathyroid hormone-(1-31)NH2 and hPTH-(1-34) in healthy humans," J Clin Endocrinol Metab. (1999) 84(8):2739-43.

Frolik, C.A. et al., "Anabolic and catabolic bone effects of human parathyroid hormone (1-34) are predicted by duration of hormone exposure," Bone (2003) 33(3):372-379.

Fujita, T., "Parathyroid hormone in the treatment of osteoporosis," BioDrugs (2001) 15(11):721-728.

Gao. Y. et al., "T cells potentiate PTH-induced cortical bone loss through CD4OL signaling," Cell Metab. (2008) 8(2):132-45.

Gensure, R.C. et al., "Parathyroid hormone and parathyroid hormone-related peptide, and their receptors," Biochem Biophys Res Commun. (2005) 328(3):666-78.

Gensure, R.C. et al., "Parathyroid hormone without parathyroid glands," Endocrinology (2005) 146(2):544-546.

Gevers, E.F. et al., "Bone marrow adipocytes; a neglected target tissue for growth hormone," Endocrinology (2002) 143(10):4065-73.

Goltzman, D., "Studies on the mechanisms of the skeletal anabolic action of endogenous and exogenous parathyroid hormone," Arch Biochem Biophys. (2008) 473(2):218-24, Epub Mar. 10, 2008.

Gopalakrishnan, R. et al., "Role of matrix Gla protein in parathyroid hormone inhibition of osteoblast mineralization," Cells Tissues Organs (2005) 181(3-4):166-75.

Gosavi, A. et al., "An unusual presentation of parathyroid adenoma—a case report," Indian J Pathol Microbiol. (2005) 48(2):208-10.

Gu, W.X. et al., "Mutual up-regulation of thyroid hormone and parathyroid hormone receptors in rat osteoblastic osteosarcoma 17/2.8 cells," Endocrinology (2001) 142(1):157-64.

Hall, A.K. et al., "The effects of parathyroid hormone on osteohlast-like cells from embryonic chick calvaria," Acta Endocrinol (Copenh). (1985) 108(2):217-23.

Han, B. at al., "Collagen-targeted BMP3 fusion proteins arrayed on collagen matrices or porous ceramics impregnated with Type I collagen enhance osteogenesis in a rat cranial defect model," J Orthopaedic Research (2002) 20;747-755.

Headley, C.M. "Hungry bone syndrome following parathyroidectomy," Anna J., (1998) 25(3):283-9; quiz 290-1.

Heath, H., 3rd, "Clinical spectrum of primary hyperparathyroidism: evolution with changes in medical practice and technology, " J Bone Miner Res. (1991) 6(Suppl 2):S63-70; discussion S83-4.

Hock, J.M. et al, "Human parathyroid hormone-(1-34) increases bone mass in ovariectomized and orchidectomized rats," Endocrinology (1988) 122(6):2899-2904.

Hock, J.M. et al., "Effects of continuous and intermittent administration and inhibition of resorption on the anabolic response of bone to parathyroid hormone," J Bone Miner Res. (1992) 7(1):65-72.

Holick, M.F. et al., "Topical PTH (1-34) is a novel, safe and effective treatment for psoriasis: a randomized self-controlled trial and an open trial," (2003) British J. Dermatology 149:370-376.

Homme, M. et al., "Differential regulation of RGS-2 by constant and oscillating PTH concentrations," Calcif Tissue Int. (2009) 84(4):305-12. Epub Feb. 20, 2009.

Horwitz, M. J. et al., "Parathyroid hormone-related protein for the treatment of postmenopausal osteoporosis: defining the maximal tolerable dose," J Clin Endocrinol Metab. (2010) 95(3):1279-87.

Horwitz, M.J. et al., "Continuous PTH and PTHrP infusion causes suppression of bone formation and discordant effects on 1,25(OH)2 vitamin D," J Bone Miner Res. (2005) 20(10):1792-803. Epub Jun. 6, 2005.

Hruska, K.A. et al., "Regulation of skeletal remodeling by parathyroid hormone," Contrib Nephrol. (1991) 91:38-42.

McCauley, L.K. et al., "Proto-oncogene c-fos is transcriptionally regulated by parathyroid hormone (PTH) and PTH-related protein in a cyclic adenosine monophosphate-dependent manner in osteoblastic cells," Endocrinology (1997) 138(12):5427-33.

McCauley, L.K. et al., "Parathyroid hormone stimulates fra-2 expression in osteoblastic cells in vitro and in vivo," Endocrinology (2001) 142(5):1975-81.

Minisola, S. et al., "Trabecular bone mineral density in primary hyperparathyroidisin: relationship to clinical presentation and biomarkers of skeletal turnover," Bone Miner. (1993) 20(2):113-23.

Minisola. S. et al., "Uneven deficits in vertebral bone density in postmenopausal patients with primary hyperparathyroidism as evaluated by posterior-anterior and lateral dual-energy absorptiometry," Osteoporos Int. (2002) 13(8):618-23.

Mitlak, B.H. et al., "Asymptomatic primary hyperparathyroidism," J Bone Miner Res. (1991) 6(Suppl 2):S103-10; discussion S121-4.

Miyachi, Y. et al., "Long-term safety and efficacy of high-concentration (20 mug/g) tacalcitol ointment in psoriasis vulgaris," Eur J Dermatol (2002) 12(5):463-468.

Morley, P. et al., "Anabolic effects of parathyroid hormone on bone," Trends Endocrinol. Metab. (1997) 8(6):225-31.

Morley, P. et al., "Parathyroid hormone: an anabolic treatment for osteoporosis," Curr Pharm Des. (2001) 7(8)671-87.

Murray, E.J. et al., "E64d, a membrane-permeable cysteine protease inhibitor, attenuates the effects of parathyroid hormone on osteoblasts in vitro," Metabolism (1997) 46(9):1090-4.

Nasu, M. et al., "Stimulatory effects of parathyroid hormone and 1,25-dihydroxyvitamin D3 on insulin-like growth factor-binding protein-5 mRNA expression in osteoblastic UMR-106 cells: the difference between transient and continuous treatments," FEBS Lett. (1997) 409(1):63-6.

Neer, R.M. et al., "Effect of parathyroid hormone (1-34) on fractures and bone mineral density in postmenopausal women with osteoporosis," N. Engl. J. Med. (2001) 344(19):1434-1441.

Nemeth, E.F., "Pharmacological regulation of parathyroid hormone secretion," Curr Pharm. Des. (2002) 8(23):2077-87.

Nilsoon, P., "Bone disease in renal failure. Clinical and histomorphometric studies," Scand J Urol Nephrol Suppl. (1984) 84:1-68.

Nishi, N. et al., "Collagen-binding growth factors: Production and characterization of functional fusion proteins having a collagen-binding domain," PNAS (1998) 95(12):7018-7023.

O'Brien, C.A. et al., "IL-6 is not required for parathyroid hormone stimulation of RANKL expression, osteoclast formation, and bone loss in mice," Am J Physiol Endocrinol Metab. (2005) 289(5):E784-93. Epub Jun. 14, 2005.

Okazaki, R., "Parathyroid hormone—its mechanisms of action and issues on clinical application," Clin Calcium. (2005) 15(5):845-51.

Olgaard, K. et al., "Can hyperparathyroid bone disease be arrested or reversed?," Clin J Am Soc Nephrol. (2006) 1(3)367-73. Epub Mar. 29, 2006.

Onyia, J.E. et al., "Molecular profile of catabolic versus anabolic treatment regimens of parathyroid hormone (PTH) in rat bone: an analysis by DNA microarray," J Cell Biochem. (2005) 95(2):403-18.

Owens, R.J. et al., "Mapping the collagen-binding site of human fibronectin by expression in *Escherichia coli*," The EMBO Journal (1986) 5(11)2825-2830.

Paillard, M. et al., "Determinants of parathormone secretion in primary hyperparathyroidism," Horm Res. (1989) 32(1-3):89-92.

Parfitt, A.M., "The actions of parathyroid hormone on bone: relation to bone remodeling and turnover, calcium homeostasis, and metabolic bone disease. Part IV of IV parts: The state of the bones in uremic hyperaparathyroidism—the mechanisms of skeletal resistance to PTH in renal failure and pseudohypoparathyroidism and the role of PTH in osteoporosis, osteopetrosis, and osteofluorosis," Metabolism. (1976) 25(10):1157-88.

Parfitt, A.M. et al., "Hypercalcemia due to constitutive activity of the parathyroid hormone (PTH)/PTH-related peptide receptor: comparison with primary hyperparathyroidism," J Clin Endocrinol Metab. (1996) 81(10):3584-8.

Peters, E.M.J. et al., "A new strategy for modulating chemotherapy-induced alopecia, using PTH/PTHrP receptor agonist and antagonist," J Invest Dermatol (2001) 117(2):173-178.

Pettway, et al., "Anabolic actions of PTH (1-34): Use of a novel tissue engineering model to investigate temporal effects on bone," Bone (2005) 36(6):959-970.

Phelps, E. et al., "Parathyroid hormone induces receptor activity modifying protein-3 (RAMP3) expression primarily via 3',5'-cyclic adenosine monophosphate signaling in osteoblasts," Calcif Tissue Int. (2005) 77(2):96-103. Epub Aug. 11, 2005.

Pirih, F.Q. et al., "Parathyroid hormone induces the NR4A family of nuclear orphan receptors in vivo," Biochem Biophys Res Commun. (2005) 332(2):494-503.

Podbesek, R. et al., "Effects of two treatment regimens with synthetic human parathyroid hormone fragment on bone formation and the tissue balance of trabecular bone in greyhounds," Endocrinology (1983) 112(3):1000-6.

Poole, K.E. et al., "Parathyroid hormone—a bone anabolic and catabolic agent," Curr Opin Pharamacol. (2005) 5(6):612-7. Epub Sep. 21, 2005.

Potter, L.K. et al., "Response to continuous and pulsatile PTH dosing: a mathematical model for parathyroid hormone receptor kinetics," Bone (2005) 37(2):159-169.

Potts, J.T., "Parathyroid hormone: past and present," J Endocronology (2005) 187:311-325.

Qin, L. et al., "Parathyroid hormone: a double-edged sword for bone metabolism," Trends Endocrinol Metab. (2004) 15(2):60-5.

Rattanakul, C. et al., "Modeling of bone formation and resorption mediated by parathyroid hormone: response to estrogen/PTH therapy" Biosystems (2003) 70(1):55-72.

Richardson, M.L. et al., "Bone mineral changes in primary hyperparathyroidism," Skeletal Radiol. (1986) 15(2):85-95.

Rickard, D.J. et al., "Intermittent treatment with parathyroid hormone (PTH) as well as a non-peptide small molecule agonist of the PTH1 receptor inhibits adipocyte differentiation in human bone marrow stromal cells," Bone (2006) 39(6):1361-1372. Epub Aug. 10, 2006.

Rixon, R.H. et al., "Parathyroid hormone fragments may stimulate bone growth in ovariectomized rats by activating adenylyl cyclase," J Bone Miner Res. (1994) 9(8):1179-89.

Robinson, J.A. et al.,"Identification of a PTH regulated gene selectively induced in vivo during PTH-mediated bone formation," J Cell Biochem. (2006) 98(5):1203-20.

Rubin, M.R. et al., "The potential of parathyroid hormone as a therapy for osteoporosis," Int J Fertil Womens Med. (2002) 47(3):103-15.

Rubin, M. et al., "The anabolic effects of parathyroid hormone," Osteoporosis International (2002) 13(4):267-277.

Rubin, M.R. et al., "The anabolic effects of parathyroid hormone therapy," Clin Geriatr Med. (2003) 19(2):415-32.

Schaefer, F., "Pulsatile parathyroid hormone secretion in health and disease," Novartis Found Symp. (2000) 227-39; discussion 239-43.

Schluter, K.-D. et al., "A N-terminal PTHrP peptide fragment void of a PTH/PTHrP-receptor binding domain activates cardiac ETA receptors," British Journal of Pharmacology (2001) 132:427-432.

Schmitt, C.P. et al., "Intermittent administration of parathyroid hormone (1-37) improves growth and bone mineral density in uremic rats," Kidney Int. (2000) 57(4):1484-92.

Schmitt, C.P. et al., "Structural organization and biological relevance of oscillatory parathyroid hormone secretion," Pediatr Nephrol. (2005) 20(3):346-51. Epub Feb. 8, 2005.

Schneider, A. et al., "Skeletal homeostasis in tissue-engineered bone," J Orthop Res. (2003) 21(5):859-64.

Ishii, H. et al., "Daily intermittent decreases in serum levels of parathyroid hormone have an anabolic-like action on the bones of uremic rats with low-turnover bone and osteomalacia," Bone (2000) 26(2):175-82.

Ishikawa, T. et al, "Delivery of a growth factor fusion protein having collagen-binding activity to wound tissues," Artif. Organs (2003) 27(2):147-154.

Ishizuya, T. at al., "Parathyroid hormone exerts disparate effects on osteoblast differentiation depending on exposure time in rat osteoblastic cells," J Clin Invest. (1997) 99(12):2961-70.

Ito, M, "Parathyroid and bone: Effect of parathyroid hormone on bone quality," Clin Calcium. (2007) 17(12):1858-64.

Jilka, R.L., "Molecular and cellular mechanisms of the anabolic effect of intermittent PTH," Bone (2007) 40(6):1434-1446. Epub Apr. 6, 2007.

Jilka, R.L. et al., "Continuous elevation of PTH increases the number of osteoblasts via both osteoclast-dependent and —independent mechanisms," J Bone Miner Res. (2010) 25(11):2427-37.

Kaji, H., "Parathyroid and bone: Effects of parathyroid hormone on bone resorption and formation: differences between intermittent and continuous treatment," Clin Calcium., (2007) 17(12):1836-42.

Kaye, M. et al., "Elective total parathyroidectomy without autotransplant in end-stage renal disease," Kidney Int. (1989) 35(6):1390-9.

Khan, A. et al., "Primary hyperparathyroidism: pathophysiology and impact on bone," Cmaj. (2000) 163(2); 184-7.

Kistler, H., "Primary hyperparathyroidism: An analysis of 152 patients with special references to acute life threatening complications (acute hyperparathyroidism)," Schweiz Med Wochenschr. (1976) 106(Suppl 3):1-61.

Kitazawa, R. et al,, "Effects of continuous infusion of parathyroid hormone and parathyroid hormone-related peptide on rat bone in vivo: comparative study by histomorphometry," Bone Miner. (1991) 12(3):157-66.

Klempa, I., "Treatment of secondary and tertiary hyperparathyroidism—surgical viewpoints," Chirurg. (1999) 70(10):1089-101.

Koh, A.J. et al., "3',5'-Cyclic adenosine monophosphate activation in osteoblastic cells: effects on parathyroid hormone-1 receptors and osteoblastic differentiation in vitro," Endocrinology (1999) 140(7):3154-62.

Komarova, S.V., "Mathematical model of paracrine interactions between osteoclasts and osteoblasts predicts anabolic action of parathyroid hormone on bone," Endocrinology. (2005) 146(8):3589-95. Epub Apr. 28, 2005.

Kousteni, S. et al., "The cell biology of parathyroid hormone in osteoblasts," Curr Osteoporos. Rep, (2008) 6(2):72-6.

Kroll, M.H, "Parathyroid hormone temporal effects on bone formation and resorption," Bull Math Biol. (2000) 62(1):163-88.

Lemaire, V. et al., "Modeling the interactions between osteoblast and osteoclast activities in bone remodeling," J Theor Biol. (2004) 229(3):293-309.

Li, X. et al., "Determination of dual effects of parathyroid hormone on skeletal gene expression in vivo by microarray and network analysis," J Biol Chem. (2007) 282(45):33086-97. Epub Aug. 9, 2007.

Liu, J. et al., "Intermittent PTH administration: a novel therapy method for periodontitis-associated alveolar bone loss," Med Hypotheses. (2009) 72(3):294-6. Epub Nov. 30, 2008.

Locklin, R.M. et al., "Mediators of the biphasic responses of bone to intermittent and continuously administered parathyroid hormone," J Cell Biochern, (2003) 89(1):180-90.

Lotinun, S. et al., "Differential effects of intermittent and continuous administration of parathyroid hormone on bone histomorphometry and gene expression," Endocrine. (2002) 17(1):29-36.

Lotinun, S. et al., "Trialzolopyrimidine (trapidil), a platelet-derived growth factor antagonist, inhibits parathyroid bone disease in an animal model for chronic hyperparathyroidism," Endocrinology, (2003) 144(5):2000-7.

Lumachi, F. et al., "Lumbar spine boen mineral density changes in patients with primary hyperparathyroidism according to age and gender," Ann N Y Acad Sci. (2007) 1117:362-6. Epub Jul. 26, 2007.

Ma, Y.L. et al., "Catabolic effects of continuous human PTH (1-38) in vivo is associated with sustained stimulation of RANKL and inhibition of osteoprotegerin and gene-associated bone formation," Endocrinology (2001) 142(9):4047-54.

Machado Do Reis, L. et al., "Accentuated osteoclastic response to parathyroid hormone undermines bone mass acquisition in osteonectin-null mice," Bone (2008) 43(2):264-73. Epub Apr. 13, 2008.

Malluche H.H. et al., "Endogenous calcitonin does not protect against hyperparathyroid bone disease in renal failure," Miner. Electrolyte Metab. (1986) 12(2):113-8.

Malluche, H.H. et al., "Osteomalacia and hyperparathyroid bone disease in patients with nephrotic syndrome," J Clin Invest. (1979) 63(3):494-500.

Malluche, H.H. et al., "Influence of the parathyroid glands on bone metabolism," Eur J Clin Invest. (2006) 36(Suppl 2):23-33.

Malluche, H.H. et al., "Effects of long-term infusion of physiologic doses of 1-34 PTH on bone" Am J Physiol. (1982) 242(2):F197-201.

Masi, L. et al., "Molecular, biochemical and cellular biology of PTH anabolic action," J Endocrinol Invest. (2005) 28(8 Suppl):37-40.

Mathias, R. et al., "Renal bone disease in pediatric and young adult patients on hemodialysis in a children's hospital," J Am Soc Nephrol. (1993) 3(12):1938-46.

Matsushita, O. et al., "A study of the collagen-binding domain of a 116-kDa *Clostridium histolyticum* collagenase," J Biological Chem (1998) 273(6):3643-3648.

Matsushita, O. et al., "Gene duplication and multiplicity of *C. histolyticum* collagenases," J. Bacteriol. (1999) 181(3):923-933.

Matsushita, O. et al., "Substrate recognition by the collagen-binding domain of *Clostridium histolyticum* class I collagenase," J of Biological Chem (2001) 276(12):8761-8770.

McCauley, L.K. et al., "PTH/PTHrP receptor is temporally regulated during osteoblast differentiation and is associated with collagen synthesis," J Cell Biochem (1996) 61:638-647.

Abdelhadi, M. et al., "Bone mineral recovery after parathyroidectomy in patients with primary and renal hyperparathyroidism," J Clin Endocrinol Metab. (1998) 83(11):3845-51.

Abe, Y. et al., "Enhancement of graft bone healing by intermittent administration of human parathyroid hormone (1-34) in a rat spinal arthrodesis model," Bone (2007) 41(5):775-785.

Abshirini, H. et al., "Pathologic fractures: a neglected clinical feature of parathyroid adenoma," Case (2010) p. 357029, Epub Nov. 29, 2010.

Aleksyniene, R. et al, "Parathyroid hormone—possible future drug for orthopedic surgery," Medicina (Kaunas) (2004) 40(9):842-9.

Andrade, M.C., et al., "Bone mineral density and bone histomorphometry in children on long-term dialysis," Pediatr Nephrol. (2007) 22(10):1767-72. Epub Aug. 7, 2007.

Barros, S.P., et al., "Parathyroid hormone protects against periodontitis-associated bone loss," J Dent Res. (2003) 82(10):791-5.

Bedi, B., et al., "Inhibition of antigen presentation and T cell costimulation blocks PTH-induced bone loss," Ann N Y Acad Sci. (2010) 1192:215-21.

Belinsky, G.S. et al,, "Direct measurement of hormone-induced acidifcation in intact bone," J Bone Miner Res., (2000) 15(3):550-6.

Bellido, T. et al., "Chronic elevation of parathyroid hormone in mice reduces expression of sclerostin by osteocytes: a novel mechanism for hormonal control of osteoblastogenesis," Endocrinology (2005) 146(11):4577-83. Epub Aug. 4, 2005.

Bergenstock, M.K. et al., "Parathyroid hormone stimulation of noncanonical Wnt signaling in bone," Ann N Y Acad Sci. (2007) 1116:354-9.

Bergwitz, C. et al., "Rapid desensitization of parathyroid hormone dependent adenylate cylase in perifused human osteosarcoma cells (SaOS-2)," Biochem Biophys Acta. (1994) 1222(3):447-56.

Bianchi, E.N. et al., "Beta-arrestin2 regulates parathyroid hormone effects on a p38 MAPK and NFkappaB gene expression network in osteoblasts" Bone (2009) 45(4):716-25. Epub Jun. 25, 2009.

Bilezikian, J.P. et al., "Asymptomatic primary hyperparathyroidism: new issues and new questions—bridging the past with the future," J Bone Miner Res. (2002) 17(Suppl 2):N57-67.

Bilezikian, J.P. et al., "Characterization and evaluation of asymptomatic primary hyperparathyroidism," J Bone Miner Res. (1991) 6(Suppl 2):S85-9; discussion S121-4.

Blachowicz, A. et al., "Serum 1-84 and 7-84 parathyroid hormone concentrations and bone in patients with primary hyperparathyroidism," Langenbecks Arch Surg. (2008) 393(5):709-13. Epub Jul. 11, 2008.

Buargub, M.A. et al., "Prevalence and pattern of renal osteodystrophy in chronic hemodialysis patients: a cross sectional study of 103 patients," Saudi J Kidney Dis Transpl. (2006) 17(3):401-7.

Calvi, L.M, et al., "Activated parathyroid hormone/parathyroid hormone-related protein receptor in osteoblastic cells differentially affects cortical and trabecular bone," J. Clin, invest. (2001)107:277-286.

Calvi, L.M. et al,, "Osteoblastic cells regulate the haematopoietic stem cell niche," Nature (2003) 425:841-846.

Canalis, E., "Effect of hormones and growth factors on alkaline phosphatase activity and collagen synthesis in cultured rat calvariae," Metabolism (1983) 32(1):14-20.

Canalis, E. et al "Insulin-like growth factor I mediates selective anabolic effects of parathyroid hormone in bone cultures," J Clin Invest. (1989) 83(1):60-5.

Chan, H.W. et al., "Prospective study on dialysis patients after total parathyroidectomy without autoimplant," Nephrology (2009) 15(4):441-7.

Chen, B et al., "Homogeneous osteogenesis and bone regeneration by demineralized bone matrix loading with collagen-targeting bone morphogenetic protein-2," Biomaterials (2007) 28:1027-1035.

\* cited by examiner

SEQUENCE LISTING

<160> NUMBER OF SEQ ID NOS: 12

<210> SEQ ID NO 1
<211> LENGTH: 158
<212> TYPE: PRT
<213> ORGANISM: Artificial
<220> FEATURE:
<223> OTHER INFORMATION: Fusion protein containing parathyroid hormone segment and collagen-binding domain

```
<400> SEQUENCE: 1

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Gly Ile Asn Ser Pro Val Tyr Pro Ile Gly Thr Glu Lys Glu Pro
        35                  40                  45

Asn Asn Ser Lys Glu Thr Ala Ser Gly Pro Ile Val Pro Gly Ile Pro
    50                  55                  60

Val Ser Gly Thr Ile Glu Asn Thr Ser Asp Gln Asp Tyr Phe Tyr Phe
65                  70                  75                  80

Asp Val Ile Thr Pro Gly Glu Val Lys Ile Asp Ile Asn Lys Leu Gly
                85                  90                  95

Tyr Gly Gly Ala Thr Trp Val Val Tyr Asp Glu Asn Asn Asn Ala Val
            100                 105                 110

Ser Tyr Ala Thr Asp Asp Gly Gln Asn Leu Ser Gly Lys Phe Lys Ala
        115                 120                 125

Asp Lys Pro Gly Arg Tyr Tyr Ile His Leu Tyr Met Phe Asn Gly Ser
    130                 135                 140

Tyr Met Pro Tyr Arg Ile Asn Ile Glu Gly Ser Val Gly Arg
145                 150                 155

<210> SEQ ID NO 2
<211> LENGTH: 251
<212> TYPE: PRT
<213> ORGANISM: Artificial
<220> FEATURE:
<223> OTHER INFORMATION: Fusion protein containing parathyroid hormone
      fragment and collagen-binding domain and polycystic kidney disease
      domain of ColH.

<400> SEQUENCE: 2

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Gly Ile Pro Glu Ile Lys Asp Leu Ser Glu Asn Lys Leu Pro Val
        35                  40                  45

Ile Tyr Met His Val Pro Lys Ser Gly Ala Leu Asn Gln Lys Val Val
    50                  55                  60

Phe Tyr Gly Lys Gly Thr Tyr Asp Pro Asp Gly Ser Ile Ala Gly Tyr
65                  70                  75                  80

Gln Trp Asp Phe Gly Asp Gly Ser Asp Phe Ser Ser Glu Gln Asn Pro
                85                  90                  95

Ser His Val Tyr Thr Lys Lys Gly Glu Tyr Thr Val Thr Leu Arg Val
            100                 105                 110

Met Asp Ser Ser Gly Gln Met Ser Glu Lys Thr Met Lys Ile Lys Ile
        115                 120                 125

Thr Asp Pro Val Tyr Pro Ile Gly Thr Glu Lys Glu Pro Asn Asn Ser
    130                 135                 140

Lys Glu Thr Ala Ser Gly Pro Ile Val Pro Gly Ile Pro Val Ser Gly
145                 150                 155                 160

Thr Ile Glu Asn Thr Ser Asp Gln Asp Tyr Phe Tyr Phe Asp Val Ile
                165                 170                 175

Thr Pro Gly Glu Val Lys Ile Asp Ile Asn Lys Leu Gly Tyr Gly Gly
            180                 185                 190
```

Ala Thr Trp Val Val Tyr Asp Glu Asn Asn Asn Ala Val Ser Tyr Ala
            195                 200                 205

Thr Asp Asp Gly Gln Asn Leu Ser Gly Lys Phe Lys Ala Asp Lys Pro
        210                 215                 220

Gly Arg Tyr Tyr Ile His Leu Tyr Met Phe Asn Gly Ser Tyr Met Pro
225                 230                 235                 240

Tyr Arg Ile Asn Ile Glu Gly Ser Val Gly Arg
            245                 250

<210> SEQ ID NO 3
<211> LENGTH: 5464
<212> TYPE: DNA
<213> ORGANISM: Artificial
<220> FEATURE:
<223> OTHER INFORMATION: Expression vector

<400> SEQUENCE: 3

| | | | | | |
|---|---|---|---|---|---|
| agcttatcga | ctgcacggtg | caccaatgct | tctggcgtca | ggcagccatc | ggaagctgtg | 60 |
| gtatggctgt | gcaggtcgta | aatcactgca | taattcgtgt | cgctcaaggc | gcactcccgt | 120 |
| tctggataat | gttttttgcg | ccgacatcat | aacggttctg | gcaaatattc | tgaaatgagc | 180 |
| tgttgacaat | taatcatcgg | ctcgtataat | gtgtggaatt | gtgagcggat | aacaatttca | 240 |
| cacaggaaac | agtattcatg | tcccctatac | taggttattg | gaaaattaag | ggccttgtgc | 300 |
| aacccactcg | acttcttttg | gaatatcttg | aagaaaaata | tgaagagcat | ttgtatgagc | 360 |
| gcgatgaagg | tgataaatgg | cgaaacaaaa | agtttgaatt | gggtttggag | tttcccaatc | 420 |
| ttccttatta | tattgatggt | gatgttaaat | taacacagtc | tatggccatc | atacgttata | 480 |
| tagctgacaa | gcacaacatg | ttgggtggtt | gtccaaaaga | gcgtgcagag | atttcaatgc | 540 |
| ttgaaggagc | ggttttggat | attagatacg | tgtttcgag | aattgcatat | agtaaagact | 600 |
| ttgaaactct | caaagttgat | tttcttagca | agctacctga | aatgctgaaa | atgttcgaag | 660 |
| atcgtttatg | tcataaaaca | tatttaaatg | gtgatcatgt | aacccatcct | gacttcatgt | 720 |
| tgtatgacgc | tcttgatgtt | gttttataca | tggacccaat | gtgcctggat | gcgttcccaa | 780 |
| aattagtttg | ttttaaaaaa | cgtattgaag | ctatcccaca | aattgataag | tacttgaaat | 840 |
| ccagcaagta | tatagcatgg | cctttgcagg | gctggcaagc | cacgtttggt | ggtggcgacc | 900 |
| atcctccaaa | atcggatctg | atcgaaggtc | gttctgtgag | tgaaatacag | cttatgcata | 960 |
| acctgggaaa | acatctgaac | tcgatggaga | gagtagaatg | gctgcgtaag | aagctgcagg | 1020 |
| atgtgcacaa | tggaattaat | tccccggtat | atccaatagg | cactgaaaaa | gaaccaaata | 1080 |
| acagtaaaga | aactgcaagt | ggtccaatag | taccaggtat | acctgttagt | ggaaccatag | 1140 |
| aaaatacaag | tgatcaagat | tatttctatt | ttgatgttat | aacaccagga | gaagtaaaaa | 1200 |
| tagatataaa | taaattaggg | tacggaggag | ctacttgggt | agtatatgat | gaaaataata | 1260 |
| atgcagtatc | ttatgccact | gatgatgggc | aaaatttaag | tggaaagttt | aaggcagata | 1320 |
| aaccaggtag | atattacatc | catctttaca | tgtttaatgg | tagttatatg | ccatatagaa | 1380 |
| ttaatataga | aggttcagta | ggaagataat | atttttattag | ttgaggtaac | tccactcgaa | 1440 |
| ttggtcgact | cgagcggccg | catcgtgact | gactgacgat | ctgcctcgcg | cgtttcggtg | 1500 |
| atgacggtga | aaacctctga | cacatgcagc | tcccggagac | ggtcacagct | tgtctgtaag | 1560 |
| cggatgccgg | gagcagacaa | gcccgtcagg | gcgcgtcagc | gggtgttggc | gggtgtcggg | 1620 |
| gcgcagccat | gacccagtca | cgtagcgata | gcggagtgta | taattcttga | agacgaaagg | 1680 |
| gcctcgtgat | acgcctattt | ttataggtta | atgtcatgat | aataatggtt | tcttagacgt | 1740 |

```
caggtggcac ttttcgggga aatgtgcgcg gaacccctat ttgtttattt ttctaaatac    1800
attcaaatat gtatccgctc atgagacaat aaccctgata aatgcttcaa taatattgaa    1860
aaaggaagag tatgagtatt caacatttcc gtgtcgccct tattcccttt tttgcggcat    1920
tttgccttcc tgttttttgct cacccagaaa cgctggtgaa agtaaaagat gctgaagatc    1980
agttgggtgc acgagtgggt tacatcgaac tggatctcaa cagcggtaag atccttgaga    2040
gttttcgccc cgaagaacgt tttccaatga tgagcacttt taaagttctg ctatgtggcg    2100
cggtattatc ccgtgttgac gccgggcaag agcaactcgg tcgccgcata cactattctc    2160
agaatgactt ggttgagtac tcaccagtca cagaaaagca tcttacggat ggcatgacag    2220
taagagaatt atgcagtgct gccataacca tgagtgataa cactgcggcc aacttacttc    2280
tgacaacgat cggaggaccg aaggagctaa ccgcttttt gcacaacatg ggggatcatg    2340
taactcgcct tgatcgttgg gaaccggagc tgaatgaagc cataccaaac gacgagcgtg    2400
acaccacgat gcctgcagca atggcaacaa cgttgcgcaa actattaact ggcgaactac    2460
ttactctagc ttcccggcaa caattaatag actggatgga ggcggataaa gttgcaggac    2520
cacttctgcg ctcggccctt ccggctggct ggtttattgc tgataaatct ggagccggtg    2580
agcgtgggtc tcgcggtatc attgcagcac tggggccaga tggtaagccc tcccgtatcg    2640
tagttatcta cacgacgggg agtcaggcaa ctatggatga acgaaataga cagatcgctg    2700
agataggtgc ctcactgatt aagcattggt aactgtcaga ccaagtttac tcatatatac    2760
tttagattga tttaaaactt catttttaat ttaaaaggat ctaggtgaag atccttttg    2820 ataatctcat gaccaaaatc ccttaacgtg agttttcgtt ccactgagcg tcagaccccg    2880
tagaaaagat caaaggatct tcttgagatc cttttttct gcgcgtaatc tgctgcttgc    2940
aaacaaaaaa accaccgcta ccagcggtgg tttgtttgcc ggatcaagag ctaccaactc    3000
tttttccgaa ggtaactggc ttcagcagag cgcagatacc aaatactgtc cttctagtgt    3060
agccgtagtt aggccaccac ttcaagaact ctgtagcacc gcctacatac ctcgctctgc    3120
taatcctgtt accagtggct gctgccagtg gcgataagtc gtgtcttacc gggttggact    3180
caagacgata gttaccggat aaggcgcagc ggtcgggctg aacggggggt tcgtgcacac    3240
agcccagctt ggagcgaacg acctacaccg aactgagata cctacagcgt gagctatgag    3300
aaagcgccac gcttcccgaa gggagaaagg cggacaggta tccggtaagc ggcagggtcg    3360
gaacaggaga gcgcacgagg gagcttccag ggggaaacgc ctggtatctt tatagtcctg    3420
tcgggtttcg ccacctctga cttgagcgtc gatttttgtg atgctcgtca ggggggcgga    3480
gcctatggaa aaacgccagc aacgcggcct ttttacggtt cctggccttt tgctggcctt    3540
ttgctcacat gttctttcct gcgttatccc ctgattctgt ggataaccgt attaccgcct    3600
ttgagtgagc tgataccgct cgccgcagcc gaacgaccga gcgcagcgag tcagtgagcg    3660
aggaagcgga agagcgcctg atgcggtatt ttctccttac gcatctgtgc ggtatttcac    3720
accgcataaa ttccgacacc atcgaatggt gcaaaacctt tcgcggtatg gcatgatagc    3780
gcccggaaga gagtcaattc agggtggtga atgtgaaacc agtaacgtta tacgatgtcg    3840
cagagtatgc cggtgtctct tatcagaccg tttcccgcgt ggtgaaccag gccagccacg    3900
tttctgcgaa aacgcgggaa aaagtggaag cggcgatggc ggagctgaat tacattccca    3960
accgcgtggc acaacaactg gcgggcaaac agtcgttgct gattggcgtt gccacctcca    4020
gtctggccct gcacgcgccg tcgcaaattg tcgcggcgat taaatctcgc gccgatcaac    4080
tgggtgccag cgtggtggtg tcgatggtag aacgaagcgg cgtcgaagcc tgtaaagcgg    4140
```

```
cggtgcacaa tcttctcgcg caacgcgtca gtgggctgat cattaactat ccgctggatg    4200
accaggatgc cattgctgtg gaagctgcct gcactaatgt tccggcgtta tttcttgatg    4260
tctctgacca gacacccatc aacagtatta ttttctccca tgaagacggt acgcgactgg    4320
gcgtggagca tctggtcgca ttgggtcacc agcaaatcgc gctgttagcg ggccattaa    4380 gttctgtctc ggcgcgtctg cgtctggctg gctggcataa atatctcact cgcaatcaaa    4440
ttcagccgat agcggaacgg gaaggcgact ggagtgccat gtccggtttt caacaaacca    4500
tgcaaatgct gaatgagggc atcgttccca ctgcgatgct ggttgccaac gatcagatgg    4560
cgctgggcgc aatgcgcgcc attaccgagt ccgggctgcg cgttggtgcg atatctcgg    4620 tagtgggata cgacgatacc gaagacagct catgttatat cccgccgtta accaccatca    4680
aacaggattt tcgcctgctg ggcaaacca gcgtggaccg cttgctgcaa ctctctcagg    4740
gccaggcggt gaagggcaat cagctgttgc ccgtctcact ggtgaaaaga aaaaccaccc    4800
tggcgcccaa tacgcaaacc gcctctcccc gcgcgttggc cgattcatta atgcagctgg    4860
cacgacaggt ttcccgactg gaaagcgggc agtgagcgca acgcaattaa tgtgagttag    4920
ctcactcatt aggcacccca ggctttacac tttatgcttc cggctcgtat gttgtgtgga    4980
attgtgagcg gataacaatt tcacacagga acagctatg accatgatta cggattcact    5040
ggccgtcgtt ttacaacgtc gtgactggga aaaccctggc gttacccaac ttaatcgcct    5100
tgcagcacat ccccctttcg ccagctggcg taatagcgaa gaggcccgca ccgatcgccc    5160
ttcccaacag ttgcgcagcc tgaatggcga atggcgcttt gcctggtttc cggcaccaga    5220
agcggtgccg gaaagctggc tggagtgcga tcttcctgag gccgatactg tcgtcgtccc    5280
ctcaaactgg cagatgcacg gttacgatgc gcccatctac accaacgtaa cctatcccat    5340
tacggtcaat ccgccgtttg ttcccacgga gaatccgacg ggttgttact cgctcacatt    5400
taatgttgat gaaagctggc tacaggaagg ccagacgcga attatttttg atggcgttgg    5460
aatt                                                                5464
```

<210> SEQ ID NO 4
<211> LENGTH: 383
<212> TYPE: PRT
<213> ORGANISM: Artificial
<220> FEATURE:
<223> OTHER INFORMATION: GST-PTH-CBD fusion protein

<400> SEQUENCE: 4

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125
```

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Ile Glu Gly
    210                 215                 220

Arg Ser Val Ser Glu Ile Gln Leu Met His Asn Leu Gly Lys His Leu
225                 230                 235                 240

Asn Ser Met Glu Arg Val Glu Trp Leu Arg Lys Lys Leu Gln Asp Val
                245                 250                 255

His Asn Gly Ile Asn Ser Pro Val Tyr Pro Ile Gly Thr Glu Lys Glu
            260                 265                 270

Pro Asn Ser Lys Glu Thr Ala Ser Gly Pro Ile Val Pro Gly Ile
        275                 280                 285

Pro Val Ser Gly Thr Ile Glu Asn Thr Ser Asp Gln Asp Tyr Phe Tyr
    290                 295                 300

Phe Asp Val Ile Thr Pro Gly Glu Val Lys Ile Asp Ile Asn Lys Leu
305                 310                 315                 320

Gly Tyr Gly Gly Ala Thr Trp Val Val Tyr Asp Glu Asn Asn Asn Ala
                325                 330                 335

Val Ser Tyr Ala Thr Asp Asp Gly Gln Asn Leu Ser Gly Lys Phe Lys
            340                 345                 350

Ala Asp Lys Pro Gly Arg Tyr Tyr Ile His Leu Tyr Met Phe Asn Gly
        355                 360                 365

Ser Tyr Met Pro Tyr Arg Ile Asn Ile Glu Gly Ser Val Gly Arg
    370                 375                 380

<210> SEQ ID NO 5
<211> LENGTH: 4
<212> TYPE: PRT
<213> ORGANISM: Artificial
<220> FEATURE:
<223> OTHER INFORMATION: Factor Xa recognition sequence

<400> SEQUENCE: 5

Ile Glu Gly Arg
1

<210> SEQ ID NO 6
<211> LENGTH: 1021
<212> TYPE: PRT
<213> ORGANISM: Clostridium histolyticum

<400> SEQUENCE: 6

Met Lys Arg Lys Cys Leu Ser Lys Arg Leu Met Leu Ala Ile Thr Met
1               5                   10                  15

Ala Thr Ile Phe Thr Val Asn Ser Thr Leu Pro Ile Tyr Ala Ala Val
                20                  25                  30

Asp Lys Asn Asn Ala Thr Ala Ala Val Gln Asn Glu Ser Lys Arg Tyr
            35                  40                  45

Thr Val Ser Tyr Leu Lys Thr Leu Asn Tyr Tyr Asp Leu Val Asp Leu

```
              50                  55                  60
Leu Val Lys Thr Glu Ile Glu Asn Leu Pro Asp Leu Phe Gln Tyr Ser
 65                  70                  75                  80

Ser Asp Ala Lys Glu Phe Tyr Gly Asn Lys Thr Arg Met Ser Phe Ile
                 85                  90                  95

Met Asp Glu Ile Gly Arg Arg Ala Pro Gln Tyr Thr Glu Ile Asp His
                100                 105                 110

Lys Gly Ile Pro Thr Leu Val Glu Val Val Arg Ala Gly Phe Tyr Leu
                115                 120                 125

Gly Phe His Asn Lys Glu Leu Asn Glu Ile Asn Lys Arg Ser Phe Lys
130                 135                 140

Glu Arg Val Ile Pro Ser Ile Leu Ala Ile Gln Lys Asn Pro Asn Phe
145                 150                 155                 160

Lys Leu Gly Thr Glu Val Gln Asp Lys Ile Val Ser Ala Thr Gly Leu
                165                 170                 175

Leu Ala Gly Asn Glu Thr Ala Pro Pro Glu Val Val Asn Asn Phe Thr
                180                 185                 190

Pro Ile Leu Gln Asp Cys Ile Lys Asn Ile Asp Arg Tyr Ala Leu Asp
                195                 200                 205

Asp Leu Lys Ser Lys Ala Leu Phe Asn Val Leu Ala Ala Pro Thr Tyr
210                 215                 220

Asp Ile Thr Glu Tyr Leu Arg Ala Thr Lys Glu Lys Pro Glu Asn Thr
225                 230                 235                 240

Pro Trp Tyr Gly Lys Ile Asp Gly Phe Ile Asn Glu Leu Lys Lys Leu
                245                 250                 255

Ala Leu Tyr Gly Lys Ile Asn Asp Asn Asn Ser Trp Ile Ile Asp Asn
                260                 265                 270

Gly Ile Tyr His Ile Ala Pro Leu Gly Lys Leu His Ser Asn Asn Lys
                275                 280                 285

Ile Gly Ile Glu Thr Leu Thr Glu Val Met Lys Val Tyr Pro Tyr Leu
                290                 295                 300

Ser Met Gln His Leu Gln Ser Ala Asp Gln Ile Lys Arg His Tyr Asp
305                 310                 315                 320

Ser Lys Asp Ala Glu Gly Asn Lys Ile Pro Leu Asp Lys Phe Lys Lys
                325                 330                 335

Glu Gly Lys Glu Lys Tyr Cys Pro Lys Thr Tyr Thr Phe Asp Asp Gly
                340                 345                 350

Lys Val Ile Ile Lys Ala Gly Ala Arg Val Glu Glu Lys Val Lys
                355                 360                 365

Arg Leu Tyr Trp Ala Ser Lys Glu Val Asn Ser Gln Phe Phe Arg Val
370                 375                 380

Tyr Gly Ile Asp Lys Pro Leu Glu Glu Gly Asn Pro Asp Asp Ile Leu
385                 390                 395                 400

Thr Met Val Ile Tyr Asn Ser Pro Glu Glu Tyr Lys Leu Asn Ser Val
                405                 410                 415

Leu Tyr Gly Tyr Asp Thr Asn Asn Gly Gly Met Tyr Ile Glu Pro Glu
                420                 425                 430

Gly Thr Phe Phe Thr Tyr Glu Arg Glu Ala Gln Glu Ser Thr Tyr Thr
                435                 440                 445

Leu Glu Glu Leu Phe Arg His Glu Tyr Thr His Tyr Leu Gln Gly Arg
                450                 455                 460

Tyr Ala Val Pro Gly Gln Trp Gly Arg Thr Lys Leu Tyr Asp Asn Asp
465                 470                 475                 480
```

-continued

Arg Leu Thr Trp Tyr Glu Glu Gly Ala Glu Leu Phe Ala Gly Ser
            485                 490                 495

Thr Arg Thr Ser Gly Ile Leu Pro Arg Lys Ser Ile Val Ser Asn Ile
            500                 505                 510

His Asn Thr Thr Arg Asn Asn Arg Tyr Lys Leu Ser Asp Thr Val His
            515                 520                 525

Ser Lys Tyr Gly Ala Ser Phe Glu Phe Tyr Asn Tyr Ala Cys Met Phe
            530                 535                 540

Met Asp Tyr Met Tyr Asn Lys Asp Met Gly Ile Leu Asn Lys Leu Asn
545                 550                 555                 560

Asp Leu Ala Lys Asn Asn Asp Val Asp Gly Tyr Asp Asn Tyr Ile Arg
                565                 570                 575

Asp Leu Ser Ser Asn Tyr Ala Leu Asn Asp Lys Tyr Gln Asp His Met
            580                 585                 590

Gln Glu Arg Ile Asp Asn Tyr Glu Asn Leu Thr Val Pro Phe Val Ala
            595                 600                 605

Asp Asp Tyr Leu Val Arg His Ala Tyr Lys Asn Pro Asn Glu Ile Tyr
            610                 615                 620

Ser Glu Ile Ser Glu Val Ala Lys Leu Lys Asp Ala Lys Ser Glu Val
625                 630                 635                 640

Lys Lys Ser Gln Tyr Phe Ser Thr Phe Thr Leu Arg Gly Ser Tyr Thr
                645                 650                 655

Gly Gly Ala Ser Lys Gly Lys Leu Glu Asp Gln Lys Ala Met Asn Lys
            660                 665                 670

Phe Ile Asp Asp Ser Leu Lys Lys Leu Asp Thr Tyr Ser Trp Ser Gly
            675                 680                 685

Tyr Lys Thr Leu Thr Ala Tyr Phe Thr Asn Tyr Lys Val Asp Ser Ser
            690                 695                 700

Asn Arg Val Thr Tyr Asp Val Phe His Gly Tyr Leu Pro Asn Glu
705                 710                 715                 720

Gly Asp Ser Lys Asn Ser Leu Pro Tyr Gly Lys Ile Asn Gly Thr Tyr
                725                 730                 735

Lys Gly Thr Glu Lys Glu Lys Ile Lys Phe Ser Ser Glu Gly Ser Phe
            740                 745                 750

Asp Pro Asp Gly Lys Ile Val Ser Tyr Glu Trp Asp Phe Gly Asp Gly
            755                 760                 765

Asn Lys Ser Asn Glu Glu Asn Pro Glu His Ser Tyr Asp Lys Val Gly
            770                 775                 780

Thr Tyr Thr Val Lys Leu Lys Val Thr Asp Lys Gly Glu Ser Ser
785                 790                 795                 800

Val Ser Thr Thr Thr Ala Glu Ile Lys Asp Leu Ser Glu Asn Lys Leu
                805                 810                 815

Pro Val Ile Tyr Met His Val Pro Lys Ser Gly Ala Leu Asn Gln Lys
            820                 825                 830

Val Val Phe Tyr Gly Lys Gly Thr Tyr Asp Pro Asp Gly Ser Ile Ala
            835                 840                 845

Gly Tyr Gln Trp Asp Phe Gly Asp Gly Ser Asp Phe Ser Ser Glu Gln
            850                 855                 860

Asn Pro Ser His Val Tyr Thr Lys Lys Gly Glu Tyr Thr Val Thr Leu
865                 870                 875                 880

Arg Val Met Asp Ser Ser Gly Gln Met Ser Glu Lys Thr Met Lys Ile
                885                 890                 895

Lys Ile Thr Asp Pro Val Tyr Pro Ile Gly Thr Glu Lys Glu Pro Asn
            900                 905                 910

```
Asn Ser Lys Glu Thr Ala Ser Gly Pro Ile Val Pro Gly Ile Pro Val
        915                 920                 925

Ser Gly Thr Ile Glu Asn Thr Ser Asp Gln Asp Tyr Phe Tyr Phe Asp
        930                 935                 940

Val Ile Thr Pro Gly Glu Val Lys Ile Asp Ile Asn Lys Leu Gly Tyr
945                 950                 955                 960

Gly Gly Ala Thr Trp Val Val Tyr Asp Glu Asn Asn Asn Ala Val Ser
                965                 970                 975

Tyr Ala Thr Asp Asp Gly Gln Asn Leu Ser Gly Lys Phe Lys Ala Asp
                980                 985                 990

Lys Pro Gly Arg Tyr Tyr Ile His Leu Tyr Met Phe Asn Gly Ser Tyr
        995                1000                1005

Met Pro Tyr Arg Ile Asn Ile Glu Gly Ser Val Gly Arg
        1010                1015                1020

<210> SEQ ID NO 7
<211> LENGTH: 84
<212> TYPE: PRT
<213> ORGANISM: Homo sapiens

<400> SEQUENCE: 7

Ser Val Ser Glu Ile Gln Leu Met His Asn Leu Gly Lys His Leu Asn
1               5                  10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly Ser
            35                  40                  45

Gln Arg Pro Arg Lys Lys Glu Asp Asn Val Leu Val Glu Ser His Glu
        50                  55                  60

Lys Ser Leu Gly Glu Ala Asp Lys Ala Asp Val Asn Val Leu Thr Lys
65                  70                  75                  80

Ala Lys Ser Gln

<210> SEQ ID NO 8
<211> LENGTH: 141
<212> TYPE: PRT
<213> ORGANISM: Homo sapiens

<400> SEQUENCE: 8

Ala Val Ser Glu His Gln Leu Leu His Asp Lys Gly Lys Ser Ile Gln
1               5                  10                  15

Asp Leu Arg Arg Arg Phe Phe Leu His His Leu Ile Ala Glu Ile His
                20                  25                  30

Thr Ala Glu Ile Arg Ala Thr Ser Glu Val Ser Pro Asn Ser Lys Pro
            35                  40                  45

Ser Pro Asn Thr Lys Asn His Pro Val Arg Phe Gly Ser Asp Asp Glu
        50                  55                  60

Gly Arg Tyr Leu Thr Gln Glu Thr Asn Lys Val Glu Thr Tyr Lys Glu
65                  70                  75                  80

Gln Pro Leu Lys Thr Pro Gly Lys Lys Lys Lys Gly Lys Pro Gly Lys
                85                  90                  95

Arg Lys Glu Gln Glu Lys Lys Lys Arg Arg Thr Arg Ser Ala Trp Leu
            100                 105                 110

Asp Ser Gly Val Thr Gly Ser Gly Leu Glu Gly Asp His Leu Ser Asp
        115                 120                 125

Thr Ser Thr Thr Ser Leu Glu Leu Asp Ser Arg Arg His
```

<210> SEQ ID NO 9
<211> LENGTH: 160
<212> TYPE: PRT
<213> ORGANISM: Artificial
<220> FEATURE:
<223> OTHER INFORMATION: Gly-Ser-PTH(1-33)-CBD fusion protein

<400> SEQUENCE: 9

```
Gly Ser Ser Val Ser Glu Ile Gln Leu Met His Asn Leu Gly Lys His
1               5                   10                  15

Leu Asn Ser Met Glu Arg Val Glu Trp Leu Arg Lys Lys Leu Gln Asp
            20                  25                  30

Val His Asn Gly Ile Asn Ser Pro Val Tyr Pro Ile Gly Thr Glu Lys
        35                  40                  45

Glu Pro Asn Asn Ser Lys Glu Thr Ala Ser Gly Pro Ile Val Pro Gly
    50                  55                  60

Ile Pro Val Ser Gly Thr Ile Glu Asn Thr Ser Asp Gln Asp Tyr Phe
65                  70                  75                  80

Tyr Phe Asp Val Ile Thr Pro Gly Glu Val Lys Ile Asp Ile Asn Lys
                85                  90                  95

Leu Gly Tyr Gly Gly Ala Thr Trp Val Val Tyr Asp Glu Asn Asn Asn
            100                 105                 110

Ala Val Ser Tyr Ala Thr Asp Asp Gly Gln Asn Leu Ser Gly Lys Phe
        115                 120                 125

Lys Ala Asp Lys Pro Gly Arg Tyr Tyr Ile His Leu Tyr Met Phe Asn
    130                 135                 140

Gly Ser Tyr Met Pro Tyr Arg Ile Asn Ile Glu Gly Ser Val Gly Arg
145                 150                 155                 160
```

<210> SEQ ID NO 10
<211> LENGTH: 152
<212> TYPE: PRT
<213> ORGANISM: Artificial
<220> FEATURE:
<223> OTHER INFORMATION: PTH(7-33)-CBD fusion protein

<400> SEQUENCE: 10

```
Leu Met His Asn Leu Gly Lys His Leu Asn Ser Met Glu Arg Val Glu
1               5                   10                  15

Trp Leu Arg Lys Lys Leu Gln Asp Val His Asn Gly Ile Asn Ser Pro
            20                  25                  30

Val Tyr Pro Ile Gly Thr Glu Lys Glu Pro Asn Asn Ser Lys Glu Thr
        35                  40                  45

Ala Ser Gly Pro Ile Val Pro Gly Ile Pro Val Ser Gly Thr Ile Glu
    50                  55                  60

Asn Thr Ser Asp Gln Asp Tyr Phe Tyr Phe Asp Val Ile Thr Pro Gly
65                  70                  75                  80

Glu Val Lys Ile Asp Ile Asn Lys Leu Gly Tyr Gly Gly Ala Thr Trp
                85                  90                  95

Val Val Tyr Asp Glu Asn Asn Asn Ala Val Ser Tyr Ala Thr Asp Asp
            100                 105                 110

Gly Gln Asn Leu Ser Gly Lys Phe Lys Ala Asp Lys Pro Gly Arg Tyr
        115                 120                 125

Tyr Ile His Leu Tyr Met Phe Asn Gly Ser Tyr Met Pro Tyr Arg Ile
    130                 135                 140

Asn Ile Glu Gly Ser Val Gly Arg
```

```
145                 150

<210> SEQ ID NO 11
<211> LENGTH: 35
<212> TYPE: PRT
<213> ORGANISM: Artificial
<220> FEATURE:
<223> OTHER INFORMATION: PTH(1-33) with Gly-Ser amino terminal extension

<400> SEQUENCE: 11

Gly Ser Ser Val Ser Glu Ile Gln Leu Met His Asn Leu Gly Lys His
1               5                   10                  15

Leu Asn Ser Met Glu Arg Val Glu Trp Leu Arg Lys Lys Leu Gln Asp
            20                  25                  30

Val His Asn
        35

<210> SEQ ID NO 12
<211> LENGTH: 6
<212> TYPE: PRT
<213> ORGANISM: Artificial
<220> FEATURE:
<223> OTHER INFORMATION: Thrombin cleavage sequence

<400> SEQUENCE: 12

Leu Val Pro Arg Gly Ser
1               5
```

FUSION PROTEINS OF COLLAGEN-BINDING DOMAIN AND PARATHYROID HORMONE

CROSS-REFERENCE TO RELATED APPLICATIONS

This patent application is a national stage filing under 35 U.S.C. 371 of International Application No. PCT/US2008/004589, filed Apr. 9, 2008, which claims priority benefits to U.S. Provisional Application No. 60/922,433, filed Apr. 9, 2007.

BACKGROUND

Osteoporosis is a bone disease characterized by thinning of bone tissue and loss of bone density over time. It is widely prevalent in the elderly. The National Osteoporosis Foundation estimates that by 2020 nearly 14 million Americans will suffer from osteoporosis. An additional 18 million may have low bone mass, or osteopenia. Osteoporosis can occur either because the body fails to make enough new bone or reabsorbs too much old bone, or both.

Osteoporosis often progresses painlessly until a bone breaks. Any bone can be affected, but one of principal concern is the hip. A hip fracture impairs a person's ability to walk and causes prolonged and sometimes permanent disability.

Osteoporosis can be treated with anabolic therapies or antiresorptive therapies. Anabolic therapies build new bone. But antiresorptive therapies do not. Instead they slow the resorption of existing bone. A major factor in the control of bone remodeling is parathyroid hormone (PTH). PTH and its analogs are the only class of anabolic therapeutics with proven clinical efficacy. Teriparatide is an approved therapeutic that is a shortened version of PTH. It consists of the N-terminal 34 amino acid residues of mature PTH (PTH(1-34)). Teriparatide is administered by once daily subcutaneous injection.

PTH is an 84-amino acid peptide. It is involved in mineral ion homeostasis. Increased PTH mobilizes calcium from bone in response to calcium deficient diets or vitamin D insufficiency. PTH also affects osteoblasts and stromal cells. Although hyperparathyroidism is associated with bone loss, PTH administration causes bone gain. PTH binds to receptors on osteoblasts, specialized bone cells that synthesize bone, and this appears to prolong osteoblast life and increase osteoblast activity, causing bone gain.

PTH-related peptide (PTHrP) is a 141-amino acid protein that is homologous to PTH over its first 13 amino acids but diverges thereafter (1-3). PTH and PTHrP act through a common PTH/PTHrP receptor.

New treatments for osteoporosis are needed. Improved methods to deliver PTH, teriparatide, or other PTH/PTHrP receptor agonist agents are needed.

SUMMARY

One embodiment disclosed herein involves compositions or bioactive agents comprising a collagen-binding polypeptide segment linked to a PTH/PTHrP receptor agonist. The inventors have constructed fusion proteins containing residues 1-33 of PTH, an active agonist fragment of PTH, fused to a collagen-binding domain (CBD) of ColH, a collagenase from *Clostridium histolyticum*. The inventors have found that the fusion protein is more active than PTH(1-34) in promoting bone growth in vivo in mice, even when administered systemically. With local administration to, for instance, a fracture site, the difference in efficacy is expected to be even greater. Peptides that are antagonists of the PTH/PTHrP receptor can also be coupled to a CBD for targeted and enhanced bioactivity.

Compositions or bioactive agents containing a collagen-binding polypeptide segment coupled to a non-peptidyl agonist or antagonist of the PTH/PTHrP receptor are also presented.

Collagen is the most abundant protein in mammals. It is the major protein component of bone and cartilage. A CBD-bioactive agent fusion protein thus targets the bioactive agent to collagen, and generally to bone and cartilage. The CBD-PTH fusion proteins have longer half-lives than PTH because of their stable binding to collagen, which tends to remove them from circulation. They can be administered locally, for instance, at a fracture site, and will tend to remain at the site of administration through binding to collagen at or near the site of administration. In support of this longer half-life, a fusion protein containing epidermal growth factor (EGF) with a CBD was shown to have much longer half life than EGF alone (8). Data is also presented in Examples 4 and 5 herein showing that a PTH-CBD fusion protein administered weekly or monthly is as effective or more effective than PTH(1-34) administered daily.

One embodiment provides a composition comprising: a collagen-binding polypeptide segment linked to a PTH/PTHrP receptor agonist; wherein the collagen-binding polypeptide segment is a bacterial collagen-binding polypeptide segment.

One embodiment provides a composition comprising: a collagen-binding polypeptide segment linked to a PTH/PTHrP receptor agonist; wherein the collagen-binding polypeptide segment is a segment of a collagenase.

One embodiment provides a composition comprising: a collagen-binding polypeptide segment linked to a PTH/PTHrP receptor agonist; wherein, over an 8-week period, the increase in bone mineral density of the composition injected with a vehicle intraperitoneally weekly in a mouse relative to the vehicle alone is at least 50% larger than the increase in bone mineral density of an equimolar amount of a composition consisting of the PTH/PTHrP agonist relative to the vehicle alone.

That is, the bioactive agent (composition) causes an increase in bone mineral density in mice when administered at an appropriate dose in a vehicle, such as an aqueous buffer solution. A control treatment with the vehicle alone may also result in some change in bone mineral density, for example because the mice are juveniles that are still growing or elderly mice whose bone mineral density is otherwise declining. The appropriate way to measure the effect of the bioactive agent is to measure increase in bone mineral density in experimental mice treated with the agent minus increase (or decrease) in bone mineral density in control mice treated with vehicle alone. This increase in bone mineral density with administration of the agent after correction for change in bone mineral density in control mice receiving vehicle alone is at least 50% larger than the increase in bone mineral density in mice treated with an agent containing only the PTH/PTHrP receptor agonist (not coupled to a collagen-binding polypeptide segment), again after correcting for any changes in bone mineral density in control mice treated with vehicle alone. For instance, in FIG. 3 herein, described in Example 4, the vehicle control mice have an increase in bone mineral density during an 8-week treatment period of 5%, mice treated with PTH(1-34) (a PTH/PTHrP agonist) have an increase in BMD of about 7.5%, and mice treated with a PTH-CBD fusion protein containing PTH(1-33) coupled to a collagen-binding domain have an increase in BMD of over 15%. The mice treated with the PTH-CBD fusion protein thus have an increase in BMD after correcting for the change with vehicle alone of over 10% (over 15% minus 5%), and the mice treated with PTH(1-34) have an increase in BMD after correcting for the change with vehicle alone of about 2.5% (about 7.5% minus 5%). Thus, intraperitoneal weekly injection of the fusion protein causes over 300% more (over 4-times as much, over 10% versus about 2.5%) increase in BMD as injection of the PTH(1-34).

Another embodiment provides a fusion protein comprising: a bacterial collagen-binding polypeptide segment; linked to a PTH/PTHrP receptor agonist polypeptide segment.

Another embodiment provides a fusion protein comprising: a collagen-binding polypeptide segment of a collagenase; linked to a PTH/PTHrP receptor agonist polypeptide segment.

Another embodiment provides a fusion protein comprising: a collagen-binding polypeptide segment; linked to a PTH/PTHrP receptor antagonist polypeptide segment.

Another embodiment provides a composition comprising: a collagen-binding polypeptide segment; linked to a non-peptidyl PTH/PTHrP receptor agonist.

Another embodiment provides a composition comprising: a collagen-binding polypeptide segment; linked to a non-peptidyl PTH/PTHrP receptor antagonist.

Another embodiment provides a composition comprising: a collagen-binding polypeptide segment; linked to a PTH/PTHrP receptor antagonist.

Another embodiment provides a method of promoting bone growth in a mammal comprising: administering to the mammal a composition comprising: (a) a collagen-binding polypeptide segment; linked to (b) a PTH/PTHrP receptor agonist.

Another embodiment provides a method of promoting bone growth in a mammal comprising: administering to the mammal a composition comprising (a) a collagen-binding polypeptide segment; linked to (b) a PTH/PTHrP receptor agonist.

Another embodiment provides a method of promoting hair growth in a mammal comprising: administering to the mammal a composition comprising: (i) a collagen-binding polypeptide segment; linked to (ii) a PTH/PTHrP receptor agonist polypeptide segment.

Another embodiment provides a method of promoting hair growth in a mammal comprising: administering to the mammal a composition comprising: (i) a collagen-binding polypeptide segment; linked to (ii) a PTH/PTHrP receptor antagonist.

Another embodiment provides a method of promoting tissue growth around an implant in a mammal comprising: administering to the mammal a composition comprising (a) a collagen-binding polypeptide segment; linked to (b) a PTH/PTHrP receptor agonist; wherein before, during, or after the step of administering the composition, the mammal receives an implant placed in contact with tissue in the mammal; and wherein the step of administering the composition is effective to promote tissue growth around the implant.

Another embodiment provides a method of promoting immune reconstitution in a mammal comprising: administering to the mammal a composition comprising: (a) a collagen-binding polypeptide segment; linked to (b) a PTH/PTHrP receptor agonist; wherein before, during, or after the step of administering the composition, the mammal receives an administration of bone marrow stem cells. The composition enhances immune reconstitution by enhancing grafting, multiplication, and/or differentiation of the bone marrow stem cells.

Another embodiment provides a method of promoting bone marrow stem cell mobilization in a mammal comprising: administering to the mammal a composition comprising: (a) a collagen-binding polypeptide segment; linked to (b) a PTH/PTHrP receptor agonist; wherein administering the composition increases the number of stem cells in circulating blood of the mammal (e.g., 7, 14, or 30 days after administering the fusion protein).

Another embodiment provides a method of treating or preventing renal osteodystrophy in a mammal comprising: administering to the mammal a composition comprising: (a) a collagen-binding polypeptide segment; linked to (b) a PTH/PTHrP receptor antagonist; wherein the mammal is afflicted with renal osteodystrophy or renal disease and the composition is effective to reduce bone loss in the mammal.

Another embodiment provides a method of treating or preventing (i.e., reducing incidence of) bone metastasis of cancer in a mammal comprising: administering to the mammal a composition comprising: (a) a collagen-binding polypeptide segment; linked to (b) a PTH/PTHrP receptor antagonist; wherein the composition is administered at a dosage effective to reduce incidence of bone metastasis of cancer or slow the growth of metastatic cancer in bone.

DETAILED DESCRIPTION

Figure 1:
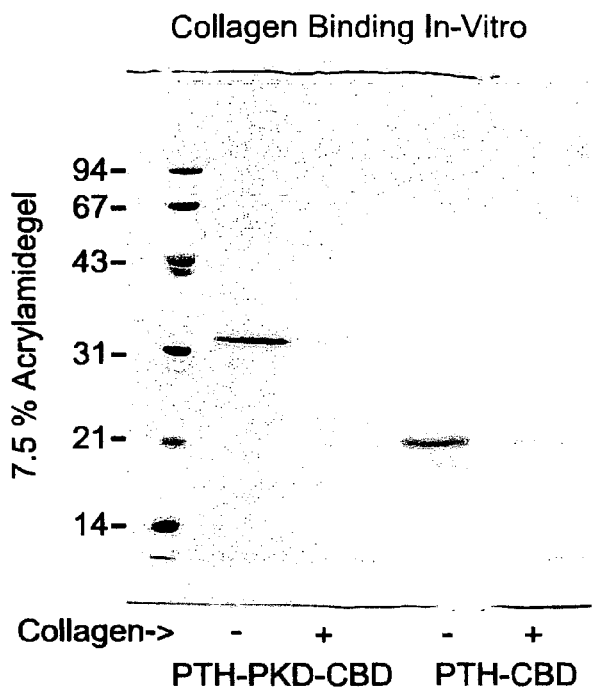
FIG. 1 is an SDS-PAGE gel showing the results of an experiment showing that two PTH-CBD fusion proteins bind to collagen.

This disclosure involves compositions, including bioactive agents and fusion proteins, comprising a collagen-binding polypeptide segment linked to a PTH/PTHrP receptor agonist or antagonist. In a preferred embodiment, the compositions are fusion proteins where the PTH/PTHrP agonist or antagonist is a polypeptide segment, where the collagen-binding polypeptide segment and PTH/PTHrP polypeptide segment are linked together in a fusion protein. But the PTH/PTHrP agonist or antagonist portion can also be a non-peptidyl agonist or antagonist.

The terms "fusion protein" and "fusion polypeptide" may be used to refer to a single polypeptide comprising two functional segments, e.g., a collagen-binding polypeptide segment and a PTH/PTHrP receptor agonist polypeptide segment. The fusion proteins may be any size, and the single polypeptide of the fusion protein may exist in a multimeric form in its functional state, e.g., by cysteine disulfide connection of two monomers of the single polypeptide. A polypeptide segment may be a synthetic polypeptide or a naturally occurring polypeptide. Such polypeptides may be a portion of a polypeptide or may comprise a mutation.

The collagen-binding polypeptide segment is a polypeptide that binds collagen and may be part of a larger fusion protein, bioactive agent, or pharmaceutical agent. Determination of whether a composition, polypeptide segment, fusion protein, or pharmaceutical or bioactive agent binds collagen can be made as described in Example 2 below. Briefly, it is incubated with collagen in binding buffer, and the mixture is then filtered through a filter that would otherwise allow it to pass through but that blocks the collagen and therefore holds back materials that bind to the collagen. The filtrate is then assayed for the presence of the composition, polypeptide segment, fusion protein, or pharmaceutical or bioactive agent. Preferably, at least 90%, more preferably at least 99% of the collagen-binding composition, polypeptide segment, fusion protein, or pharmaceutical or bioactive agent is retained by the filter in this assay, as compared to when the filtration is performed without collagen.

One embodiment disclosed herein involves fusion proteins comprising a collagen-binding polypeptide segment linked to a PTH/PTHrP receptor agonist polypeptide segment.

The PTH/PTHrP receptor agonist polypeptide segment may be a synthetic polypeptide or a naturally occurring polypeptide. Such polypeptides may be a portion of a polypeptide or may comprise a mutation. Agonist activity with the PTH/PTHrP receptor can be assayed as described in Example 3 below by a cAMP stimulation assay. An agonist will stimulate cAMP synthesis. Preferably, an agonist can activate receptor activity at least 10% as much as PTH(1-34).

In a specific embodiment when injected intraperitoneally weekly in mice the agonist fusion protein causes at least 50% more increase in bone mineral density (as compared to vehicle control) than an equimolar amount of a polypeptide consisting of the PTH/PTHrP receptor agonist polypeptide segment when injected intraperitoneally weekly (as compared to vehicle control) over an 8-week period (as in Example 4 below). Likewise, in other specific embodiments, the fusion protein causes a statistically significantly ($p<0.05$) greater increase in BMD, or at least twice as much increase in BMD, than an equimolar amount of a polypeptide consisting of the PTH/PTHrP receptor agonist polypeptide segment or than PTH(1-34).

In some embodiments of the fusion proteins, the collagen-binding polypeptide segment is a bacterial collagen-binding polypeptide segment. In a more specific embodiment, it is a *Clostridium* collagen-binding polypeptide segment.

In some embodiments of the fusion proteins, the collagen-binding polypeptide segment is a segment of a collagenase, or a bacterial collagenase, or a *Clostridium* collagenase. Preferably the segment is only a portion of the collagenase and the collagen-binding polypeptide segment does not have collagenase activity.

In some embodiments, the collagenase is ColH, SEQ ID NO:6.

In some embodiments, the collagen-binding polypeptide segment is or includes residues 901-1021 of SEQ ID NO:6 (residues 38-158 of SEQ ID NO:1), or a fragment of residues 38-158 of SEQ ID NO:1 at least 8 amino acid residues in length.

In some embodiments, the collagen-binding polypeptide segment is at least 90%, at least 95%, at least 96%, at least 98%, or at least 99% identical to residues 38-158 of SEQ ID NO:1.

In some embodiments, the collagen-binding polypeptide segment is or includes residues 807-1021 of SEQ ID NO:6 (residues 37-251 of SEQ ID NO:2).

In specific embodiments, the collagen-binding polypeptide segment is or comprises a fragment of residues 901-1021 of SEQ ID NO:6, e.g., a fragment of at least 8, at least 10, at least 20, at least 30 at least 40, or at least 50 consecutive amino acid residues of residues 901-1021 of SEQ ID NO:6.

Among other proteins the collagen-binding segment can be derived from are ColG (5), a class I collagenase from *Clostridium histolyticum*. ColH is a class II collagenase (6).

The collagen-binding polypeptide segment may also be a polypeptide segment from bone sialoprotein, fibronectin, or von Willebrand factor, as described in references (30-33), or may be polyglutamic acid (34).

In specific embodiments, the PTH/PTHrP receptor agonist polypeptide segment is a PTH or PTHrP polypeptide segment. One human isoform of PTH is SEQ ID NO:7. One human isoform of PTHrP is SEQ ID NO:8.

In specific embodiments, the PTH/PTHrP receptor agonist polypeptide segment is or includes residues 1-33 of SEQ ID NO:1 (residues 1-33 of PTH (SEQ ID NO:7)).

In specific embodiments, the PTH/PTHrP receptor agonist polypeptide segment is or includes residues 1-34 of PTH (SEQ ID NO:7). In other embodiments, it is a fragment of residues 1-34 of PTH (SEQ ID NO:7).

In specific embodiments, the PTH/PTHrP receptor agonist polypeptide segment is or includes residues 1-84 of PTH (SEQ ID NO:7).

In specific embodiments, the PTH/PTHrP receptor agonist polypeptide segment is or includes residues 1-14 of PTH (SEQ ID NO:7).

In specific embodiments, the PTH/PTHrP receptor agonist is a PTH or PTHrP polypeptide segment.

In one embodiment, the PTH/PTHrP receptor agonist polypeptide segment is N terminal to the collagen-binding polypeptide segment in the fusion protein. That is, the two polypeptide segments each have an N-terminal and a C-terminal, and the N-terminal of the collagen-binding polypeptide segment is linked directly or through a linker polypeptide segment to the C-terminal of the PTH/PTHrP agonist polypeptide segment.

The two polypeptide segments of the fusion proteins can be linked directly or indirectly. For instance, the two segments may be linked directly through, e.g., a peptide bond or chemical cross-linking, or indirectly, through, e.g., a linker segment or linker polypeptide.

This disclosure also provides a fusion protein comprising a collagen-binding polypeptide segment linked to a PTH/PTHrP receptor antagonist polypeptide segment.

The PTH/PTHrP receptor antagonist polypeptide segment may be a synthetic polypeptide or a naturally occurring polypeptide. Such polypeptides may be a portion of a polypeptide or may comprise a mutation. Antagonist activity with the PTH/PTHrP receptor can be assayed as described in Example 3 below by a cAMP stimulation assay. An antagonist will inhibit stimulation of cAMP synthesis by PTH(1-34). Preferably, when mixed with PTH(1-34), the antagonist can inhibit activation of the receptor by PTH(1-34) by at least 50%. In contrast, when not mixed with PTH, the antagonist activates the receptor by less than 5% of the receptor's maximal activation by PTH(1-34).

In the fusion proteins containing a PTH/PTHrP receptor antagonist, the collagen-binding polypeptide segment can be the same segments as found in the fusions containing a PTH/PTHrP receptor agonist.

In some embodiments, the PTH/PTHrP receptor antagonist is a PTH or PTHrP polypeptide segment.

The PTH/PTHrP receptor antagonist can include in one embodiment PTH(7-34), i.e., residues 7-34 of PTH (SEQ ID NO:7). In another embodiment, it is or includes residues 7-33 of PTH (SEQ ID NO:7). In other embodiments, it is a fragment of residues 7-34 of SEQ ID NO:8.

In another embodiment, the PTH/PTHrP receptor antagonist includes PTH(7-14), i.e., residues 7-14 of PTH (SEQ ID NO:7).

In another embodiment, the PTH/PTHrP receptor antagonists include residues 1-14 of PTH with an N-terminal extension. Adding an N-terminal extension to PTH or active N-terminal fragments of PTH converts the PTH peptides to antagonists. The N-terminal extension can be 1, 2, 3, 4, 5, or more amino acids in length. The identity of the amino acids in the N-terminal extension is typically not important. In one embodiment, the PTH/PTHrP receptor antagonist includes residues 1-33 of PTH with a Gly-Ser extension at the N-terminus (SEQ ID NO:11).

In another embodiment, the PTH/PTHrP receptor antagonist includes PTHrP(7-34), i.e., residues 7-34 of SEQ ID NO:8, or a fragment of residues 7-34 of SEQ ID NO:8.

In another embodiment, the PTH/PTHrP receptor antagonist includes mouse TIP(7-39) (reference 18). Other PTH/PTHrP receptor antagonists that may be used in the fusion proteins are also disclosed in reference (18).

In one embodiment, the PTH/PTHrP receptor antagonist polypeptide segment is N terminal to the collagen-binding polypeptide segment in the antagonist fusion protein. That is, the two polypeptide segments each have an N-terminal and a C-terminal, and the N-terminal of the collagen-binding polypeptide segment is linked directly or through a linker polypeptide segment to the C-terminal of the PTH/PTHrP antagonist polypeptide segment.

As with the agonist, the two polypeptide segments of the antagonist fusion proteins can be linked directly or indirectly.

This disclosure also provides a method of promoting bone growth in a mammal involving administering to the mammal a fusion protein comprising a collagen-binding polypeptide segment linked to a PTH/PTHrP agonist polypeptide segment.

In particular embodiments, administering the fusion protein to the mammal increases trabecular bone mineral volume and/or trabecular bone mineral density or slows loss of trabecular bone mineral volume and/or trabecular bone mineral density.

In particular embodiments, administering the fusion protein to the mammal increases cortical bone mineral volume and/or cortical bone mineral density or slows loss of cortical bone mineral volume and/or cortical bone mineral density.

Bone mineral volume is visible from histologic staining of slides. The term "bone mineral volume" as used herein refers to the volume occupied by mineralized bone. "Bone mineral density" as used herein refers to areal bone density, i.e., the amount of bone mineral per unit 2-dimensional area of bone. It can be measured by x-rays, or DEXA (Example 4 below).

The inventors have found that the PTH-CBD fusion protein increases both the bone mineral volume and density of both trabecular and cortical bone. The effect on cortical bone is surprising, because PTH(1-34) has been shown to have little effect on cortical bone mineral density or even decrease cortical bone mineral density, even as it increases trabecular bone mineral density (25-27).

The fusion protein can be administered systemically, e.g., by intravenous injection. The inventors have found that when administering the fusion protein subcutaneously it binds locally at the site of injection if the fusion protein is dissolved in neutral pH buffer. But if the fusion protein is dissolved in pH 4.5 or below buffer, the collagen-binding domain does not bind collagen, and the fusion protein has time to disperse systemically before it binds collagen elsewhere in the body at neutral pH. Thus, in one embodiment, systemic administration of the fusion proteins involves administering the fusion protein dissolved in buffer or aqueous solution at a pH lower than about 5.0 or at pH 4.5 or below. In another embodiment, systemic administration of the fusion proteins involves administering the fusion proteins dissolved in aqueous solution at pH lower than about 6.0.

In particular embodiments, the fusion protein is administered by injection, e.g., intravenous or subcutaneous or intraperitoneal injection. Administration by injection may be systemic administration or local administration.

In particular embodiments, the fusion protein is administered in an orthopedic implant. Examples of orthopedic implants in which the fusion protein may be administered include an orthopedic bone void filler, an adjunct to bone fracture stabilization, an intramedullary fixation device, a joint augmentation/replacement device, a bone fixation plate, a screw, a tack, a clip, a staple, a nail, a pin, a rod, an anchor, a screw augmentation device, or a cranial reconstruction device. Another example of an orthopedic implant is a dental implant. Examples of dental implants include an artificial tooth root replacement, implant-supported bridges and dentures. Other examples will be known to those of skill in the art.

To be administered in an implant, as used herein, means that the fusion protein may be associated with the implant, by for instance, adhesion, covalent or non-covalent bonding to the surface of the implant, entrapment in pores of a polymer coating of an implant, or mixing with a component of the implant, such as ceramic particles. If the ceramic particles are porous, the fusion protein can be entrapped in the pores. By "entrapped in the pores" it is meant that diffusion of the fusion protein out of the material is slowed due to the pore structure, not necessarily that the fusion protein cannot diffuse out of the material until the material breaks down.

For instance, the fusion protein can be entrapped in a biodegradable polymer as described in U.S. Pat. No. 7,060,299. It may be formed into particles with a polysaccharide gum, and then the particles entrapped in a matrix of a polymer as described in U.S. Pat. No. 7,060,299. The polymer can be formed as a coating on the surface of an implant.

The fusion protein can also be bonded to a surface such as gold on an implant through sulfhydryls of the protein, as described in U.S. Pat. No. 6,428,579.

The fusion protein can be mixed with a ceramic or with ceramic particles, including for example hydroxyapatite or tricalcium phosphate, both of which are often used as fillers for bone remodeling (U.S. Published Patent Application No. 20030091609).

A porous polymer can be formed by forming the polymer in an organic solvent with particles of a material that is not soluble in the organic solvent, such as salt or sugar crystals. After the polymer is cured, the particles can be removed to expose the open pores by washing the polymer matrix in an aqueous solution that solubilizes the salt or sugar particles. Incubating the polymer matrix with a solution of the fusion protein can allow the fusion protein to diffuse into the pores of the polymer and become entrapped therein (U.S. Published Patent Application No. 20030091609).

Other methods of adhering proteins to a surface of a material are disclosed in U.S. Pat. No. 6,617,142. Still other methods are available to those of skill in the art.

The fusion protein can be mixed with demineralized bone matrix (DBM). Demineralized bone matrices are prepared by acid extraction of allograft bone, resulting in loss of most of the mineralized component but retention of collagen and noncollagenous proteins, including growth factors. DBM is used as a bone-graft substitute or extender. Since DBM contains extensive amounts of collagen, the fusion proteins will bind to the collagen of DBM if mixed with DBM in binding buffer.

In specific embodiments, the orthopedic implant includes hydroxyapatite, tricalcium phosphate, or demineralized bone matrix. In other embodiments, the orthopedic implant includes a polymer. Many natural and synthetic polymers may be included in an orthopedic implant (e.g., as a coating). Examples of natural porous polymers include gelatin, fibrin, collagen, elastin, hyaluronic acid, chondroitin sulfate, dermatan sulfate, heparin sulfate, heparin, cellulose, chitin, chitosan, mixtures or copolymers thereof, or a wide variety of others typically disclosed as being useful in implantable medical devices. Examples of synthetic porous polymers include silicone, polyurethane, polysulfone, polyethylene, polypropylene, polyamide, polyester, polycarboxylic acids, polyvinylpyrrolidone (PVP), maleic anhydride polymers, polyamides, polyvinyl alcohols (PVA), polyethylene oxides, polyacrylic acid polymers, polytetrafluoroethylene, polyhydroxyethylmethacrylic acid (pHEMA), polyaminopropylmethacrylamide (pAPMA), polyacrylamido-2-methylpropanesulf-onic acid (pAMPS), polyacrylamide, polyacrylic acid, mixtures or copolymers thereof, or a wide variety of others typically disclosed as being useful in implantable medical devices. Additional examples of synthetic porous polymers include biodegradable synthetic porous polymers, such as polyglycolic acid, polylactic acid, polydiaxonone, poly(,-caprolactone), polyanhydrides, poly(3-hydroxybutyrate), poly(ortho esters), poly(amino acids), polyiminocarbonates, and mixtures or copolymers thereof.

Thus, another embodiment provides a method of promoting tissue growth around an implant in a mammal comprising: administering to the mammal a fusion protein comprising: (a) a collagen-binding polypeptide segment; linked to (b) a PTH/PTHrP receptor agonist polypeptide segment. Before, during, or after the step of administering the fusion protein, the mammal receives an implant placed in contact with tissue in the mammal; and the step of administering the fusion protein is effective to promote tissue growth around the implant. The tissue growth promoted around the implant may be bone, cartilage, or other tissue. In one embodiment, it may be skin.

In a particular embodiment, the step of administering the fusion protein comprises placing an implant in contact with tissue in the mammal, wherein the implant comprises the fusion protein.

In a particular embodiment, the implant is a dental implant.

In another embodiment, the implant is a bone graft.

In other embodiments, the implant is an orthopedic bone void filler, an adjunct to bone fracture stabilization, an intramedullary fixation device, a joint augmentation/replacement device, a bone fixation plate, a screw, a tack, a clip, a staple, a nail, a pin, a rod, an anchor, a screw augmentation device, or a cranial reconstruction device.

In specific embodiments, the implant comprises intact bone. Here, in one embodiment, the implant is incubated with the fusion protein for a time sufficient to allow the fusion protein to bind to collagen in the intact bone before implanting the implant in the mammal.

In specific embodiments, the implant comprises bone cement, hydroxyapatite, or demineralized bone.

In specific embodiments, the implant comprises osteoblasts.

In specific embodiments, the implant is predominantly plastic, metal, or ceramic (i.e., the majority of its mass is plastic, metal, or ceramic material).

Another embodiment provides a method of promoting hair growth in a mammal comprising: administering to the mammal a fusion protein comprising: a collagen-binding polypeptide segment; linked to a PTH/PTHrP receptor agonist polypeptide segment.

We have found that fusion proteins containing the receptor agonists were more effective than those containing receptor antagonists in promoting hair growth in mice treated with cyclophosphamide to induce chemotherapy-induced alopecia (Example 8 below). A fusion protein containing a PTH/PTHrP receptor antagonist was also tested and also induced some hair growth, but the hair that grew appeared less thick (data not shown). Thus, fusion proteins containing either a PTH/PTHrP receptor agonist or antagonist can be used to promote hair growth, but fusion proteins containing a receptor agonist are preferred for chemotherapy-induced alopecia.

To promote hair growth, the fusion proteins may be administered locally at a desired site of hair growth, e.g., by subcutaneous or intradermal injection. The fusion proteins will bind to collagen in the skin near the site of subcutaneous or intradermal injection and remain bound at the site for long-lasting effect. The fusion proteins can also be administered systemically to promote hair growth. This is preferred to treat chemotherapy-induced alopecia.

In one embodiment of the method of promoting hair growth, the mammal is afflicted with chemotherapy-induced alopecia.

Another embodiment provides a method of promoting immune reconstitution in a mammal comprising: administering to the mammal a fusion protein comprising: (a) a collagen-binding polypeptide segment; linked to (b) a PTH/PTHrP receptor agonist polypeptide segment; wherein before, during, or after administering the fusion protein, the mammal receives an administration of bone marrow stem cells. As used here, the term "bone marrow stem cells" may refer to any stem cells that can implant in bone marrow and differentiate into a variety of types of lymphocytes. Thus, the stem cells may be obtained, for instance, from umbilical cord blood, embryos, the mammal's own blood or bone marrow, or another mammal's blood or bone marrow. Administration of the fusion protein is expected to show an increase in survival following bone marrow ablation and a stem cell transplant in mice. It is also expected to increase the rate of neutrophil number increase—i.e., neutrophil numbers are greater at specific time points (e.g., 7, 14, 21, or 30 days) after transplant in patients or experimental animals receiving the fusion protein in conjunction with the stem cell transplant than in a comparison group not receiving the fusion protein.

In one embodiment, the stem cells will be umbilical cord blood stem cells. Umbilical cord blood is an especially useful alternative for patients in need of a stem cell transplant who do not have an MHC-matched related or unrelated donor. But the number of stem cells in a single unit of umbilical cord blood is often insufficient for successful engraftment after a bone marrow stem cell transplant (10). Administration of the fusion protein disclosed herein containing a PTH/PTHrP receptor agonist is expected to improve grafting of the stem cells and increase the odds of a successful graft with one or two units of umbilical cord blood.

In another embodiment, the stem cells will be autologous blood stem cells. Often too few stem cells are mobilized from a patient to support autologous stem cell transplant. Administering the fusion protein is expected to enhance the chance of successful engraftment when the number of stem cells transplanted is less than optimal. It also is expected to enhance the chance of successful engraftment when the number of stem cells transplanted is considered adequate.

Preferably the fusion protein would be administered before or together with administration of the stem cells to promote engraftment of stem cells in the bone marrow. But it may also be administered after administration of the stem cells.

Another embodiment provides a method of promoting bone marrow stem cell mobilization in a mammal comprising: administering to the mammal a fusion protein comprising: (a) a collagen-binding polypeptide segment; linked to (b) a PTH/PTHrP receptor agonist polypeptide segment. Administering the fusion protein is expected to increase the number of stem cells in circulating blood of the mammal (e.g., 7, 14, or 30 days after administering the fusion protein). In a specific embodiment, this method further comprises collecting stem cells from blood of the mammal after the step of administering the fusion protein to the mammal.

Autologous stem cell transplantation cures lymphomas in many patients and improves survival in multiple myeloma. But approximately 20% of patients do not mobilize sufficient stem cells to safely support autologous stem cell transplantation (11). The fusion protein described herein containing a PTH/PTHrP receptor agonist is expected to promote stem cell mobilization.

Another embodiment is expected to provide a method of treating myocardial infarction in a mammal comprising: administering to a mammal after the mammal suffers a myocardial infarction a fusion protein comprising: (a) a collagen-binding polypeptide segment; linked to (b) a PTH/PTHrP receptor agonist polypeptide segment.

Another embodiment provides a method of treating or preventing renal osteodystrophy in a mammal comprising: administering to the mammal a fusion protein comprising: (a) a collagen-binding polypeptide segment; linked to (b) a PTH/PTHrP receptor antagonist polypeptide segment; wherein the mammal is afflicted with renal osteodystrophy or renal disease. In this embodiment, the fusion protein is expected to be effective to reduce bone loss in the mammal.

One embodiment is expected to provide a method of treating or reducing incidence of bone metastasis of cancer in a mammal comprising: administering to the mammal a fusion protein comprising: (a) a collagen-binding polypeptide segment; linked to (b) a PTH/PTHrP receptor antagonist polypeptide segment.

PTHrP is positively associated with bone metastasis (15, 16, 17). Breast carcinoma metastatic to bone expresses PTHrP in more than 90% of cases, compared with 17% in metastases to nonbone sites (15). In a mouse model, human tumor cells transfected with a cDNA to overexpress human PTHrP had increased metastasis to bone (15). Conversely, administration of an anti-PTHrP antibody decreased bone metastases (15, 17).

Binding of PTHrP to its receptor alters the microenvironment of bone favorably to promote metastasis. A fusion protein containing a CBD segment and a PTH/PTHrP receptor antagonist will likely occupy the receptor in bone and thus decrease the occurrence of metastasis. It is expected to slow the growth of metastic tumors in bone.

In all the embodiments described herein, fusion proteins comprising (a) a collagen-binding polypeptide segment linked to (b) a PTH/PTHrP receptor agonist polypeptide segment can be replaced by pharmaceutical agents comprising (a) a collagen-binding polypeptide segment linked to (b) a PTH/PTHrP receptor agonist or a non-peptidyl PTH/PTHrP receptor agonist. An example of a non-peptidyl PTH/PTHrP receptor agonist is compound AH3960 (19).

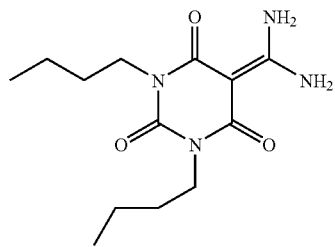

AH3960

AH3960 contains two amino groups. These can be used to cross-link the compound to amino groups on the collagen-binding polypeptide segment through a cross-linker such as DSG (disuccinimidyl glutarate) or through the combination of SANH (succinimidyl-4-hydrazinonicotinate acetone hydrazone) and SFB (succinimidyl-4-formyl benzoate). AH3960 can be cross-linked through its amino group to a carboxyl group of the collagen-binding polypeptide segment by EDC (1-ethyl-3-[3-dimethylaminopropyl]carbodiimide hydrochloride). These products are available from Pierce (piercenet.com, Thermo Fisher Scientific Inc., Rockford, Ill.). Protocols and reaction conditions are also available in the product literature from Pierce (piercenet.com).

Likewise, in the embodiments described herein involving receptor antagonist fusion proteins, fusion proteins comprising (a) a collagen-binding polypeptide segment linked to (b) a PTH/PTHrP receptor antagonist polypeptide segment can be replaced by pharmaceutical agents comprising (a) a collagen-binding polypeptide segment linked to (b) a PTH/PTHrP receptor antagonist or a non-peptidyl PTH/PTHrP receptor antagonist.

Thus, another embodiment provides a pharmaceutical agent comprising: (a) a collagen-binding polypeptide segment linked to (b) a PTH/PTHrP receptor antagonist, where the antagonist may be non-peptidyl. Non-peptidyl antagonists of the PTH/PTHrP receptor include compounds disclosed in (20), including compound 2 below:

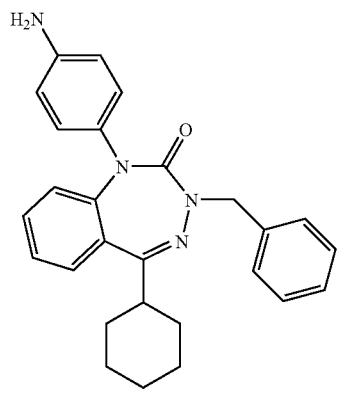

2

Compound 2 can be coupled through its amino group to amino or carboxyl groups of the collagen-binding polypeptide segment as described above for compound AH3960. In compound 3 of reference (20), the amino group of compound 2 is replaced with a carboxyl group. This can be coupled to amino groups of the collagen-binding polypeptide segment with EDC.

In another embodiment of the pharmaceutical agents comprising (a) a collagen-binding polypeptide segment; linked to (b) a PTH/PTHrP receptor agonist polypeptide segment or antagonist polypeptide segment, segment (a) and segment (b) are separate polypeptides, and the two polypeptides are linked by chemical cross-linking. The two polypeptides can be cross-linked through amino groups by reagents including DSG (disuccinimidyl glutarate) or glutaraldehyde. They can also be cross-linked through amino groups by derivatizing one polypeptide with SANH (succinimidyl-4-hydrazinonicotinate acetone hydrazone) and the other with SFB (succinimidyl-4-formyl benzoate), and then mixing the two derivatized polypeptides to cross-link. The two polypeptides can be cross-linked between an amino group of one polypeptide and a carboxyl of the other by reaction with EDC (1-ethyl-3-[3-dimethylaminopropyl]carbodiimide hydrochloride). The polypeptides can also be cross-linked (e.g., covalently coupled) by any other suitable method known to a person of ordinary skill in the art. These cross-linking reagents are available from Pierce (piercenet.com, Thermo Fisher Scientific Inc., Rockford, Ill.). Protocols and reaction conditions are also available in the product literature from Pierce (piercenet.com). These and other applicable cross-linking methods are described in U.S. published patent applications 20060258569 and 20070224119.

Based on the data herein, the individual doses of pharmaceutical agents comprising a collagen-binding polypeptide segment linked to a PTH/PTHrP receptor agonist polypeptide segment can be approximately the same on a molar basis as doses used for PTH(1-34). But the pharmaceutical agents comprising a collagen-binding polypeptide segment linked to a PTH/PTHrP receptor agonist polypeptide segment can be administered less frequently, because linking the agonist to the collagen-binding polypeptide segment gives it much more prolonged activity in vivo.

The following examples are presented to illustrate various aspects of the disclosure without limiting the scope thereof.

EXAMPLES

Example 1

Expression of PTH-Collagen-Binding Domain Fusion Proteins

A plasmid expressing a PTH-CBD fusion protein was constructed by inserting the PTH-CBD coding sequence into pGEX-5X-1 (GE Lifesciences). The sequence of the resulting plasmid is SEQ ID NO:3. Nucleotides 258 to 1409 of SEQ ID NO:3 encode a fusion protein containing glutathione-S-transferase (GST) fused at its C terminus to a PTH-CBD fusion protein. SEQ ID NO:4 is the full encoded GST-PTH-CBD fusion protein. Residues 222-225 are IEGR (SEQ ID NO:5), a factor Xa protease recognition site. Residues 226-383 of SEQ ID NO:4 correspond to SEQ ID NO:1 and are the PTH-CBD fusion protein. Factor Xa cleaves after the Arg that is amino acid residue 225 of SEQ ID NO:4 to release SEQ ID NO:1, the PTH-CBD fusion protein. Residues 1-33 of SEQ ID NO:1 are the N-terminal 33 residues of PTH. Residues 38-158 are a collagen-binding domain (CBD) of the ColH collagenase of *Clostridium histolyticum*. The CBD of the fusion protein corresponds to residues 901-1021 of ColH (SEQ ID NO:6). Residues 34-37 of SEQ ID NO:1 are a linker segment.

A second PTH-CBD fusion protein, PTH-PKD-CBD (SEQ ID NO:2), was expressed from the a plasmid otherwise identical to SEQ ID NO:3 with a longer insert segment from the colH gene to express. Like SEQ ID NO:1, it was expressed as part of a GST fusion protein and cleaved from GST by Factor Xa. Residues 1-33 of SEQ ID NO:2 are the N-terminal 33 residues of PTH. Residues 34-36 are a linker segment. And residues 37-251 are residues 807-1021 of ColH. This fusion protein includes a polycystic kidney disease (PKD) domain of ColH (residues 807-900 of ColH), in addition to the collagen binding domain of residues 901-1021 of ColH found in both SEQ ID NO:1 and SEQ ID NO:2. It was thought that including the PKD domain might minimize domain-domain interferences or other steric hindrances between the PTH domain and CBD domain.

Purification of CBD Fusion Proteins—*E. coli*

BL21 was transformed with the recombinant plasmids. Each clone was grown in one liter of 2YT-G medium to an optical density at 600 nm of 0.7. Isopropyl-1-thio-beta-D-galactopyranoside was added to a final concentration of 0.1 mM, and cells were grown for a further 2 hours. In order to prevent proteolyis during the purification procedures, phenylmethylsulfonylfluoride was added to the culture to a final concentration of 1 mM. Cells were harvested by centrifugation, and disrupted in a French pressure cell. Cell debris was removed by centrifugation, and the cleared lysate was used for the purification of the fusion protein by a batch method using glutathione-SEPHAROSE 4B beads (volume, 4-ml;

GE Lifesciences) as described by the manufacturer. The GST-tag of each fusion protein was cleaved by incubation with Factor Xa (New England Biolabs, 0.2 µg/mg of fusion protein) for 20 h at room temperature. The cleaved protein fractions were dialyzed three times against 1 liter of 50 mM Tris-HCl (pH7.5), 100 mM NaCl at 4° C. to remove glutathione. The N-terminal GST fragment was removed by applying the fraction to a glutathione-SEPHAROSE 4B column (bed volume, 2 ml). Ten amino acid residues from the N terminus were confirmed for each fragment on an automatic protein sequencer (Model 492, Perkin-Elmer). The molecular mass of the purified C-terminal fragment was confirmed by matrix-assisted laser desorption time-of-flight mass spectrometry (MALDI-TOF MS).

Example 2

Demonstration of Collagen Binding by the PTH-CBD Fusion Proteins

Five mg insoluble collagen type I, (C-9879; Sigma) was added to an ULTRA FREE micro centrifugal device, 0.22 micrometer low-binding DURAPORE membrane (Millipore, Bedford, Mass.) and placed in a micro centrifuge tube (Catalogue No:UFC30GV00-Millipore). All steps were carried out at room temperature unless otherwise specified. Collagen binding buffer (200 microliters) (50 mM Tris-HCl, pH 7.5, 5 mM $CaCl_2$) was added to swell the collagen fibers. After incubation for 30 minutes, the tube was centrifuged at 15,000 g for 15 minutes. Centrifugation was repeated after changing the direction of the tube in the rotor. The collagen precipitate was resuspended in 60 mcl of collagen binding buffer containing 100 pmole of fusion protein and incubated for 30 minutes. The mixture was then centrifuged through the device at 15,000×g for 15 minutes. Proteins bound to the collagen would be retained by the filter along with the collagen. Proteins that do not bind to collagen would pass through in the filtrate. The filtrate was analyzed by SDS-PAGE.

FIG. 1 shows a photograph of the SDS-PAGE gel. Lane 1 on the left is molecular weight markers. Lane 2 is the filtrate of a mixture containing PTH-PKD-CBD fusion protein filtered without collagen. Lane 3 shows the filtrate of a mixture of PTH-PKD-CBD fusion protein with collagen. Lanes 4 and 5 show the filtrate of the PTH-CBD fusion protein incubated without and with collagen, respectively. The result shows that both fusion proteins failed to pass through the filter when incubated with collagen, but did pass through when incubated without collagen. This shows both fusion proteins bound to collagen.

Example 3

In Vitro Biological Activity of PTH-CBD Fusion Proteins

HKrK-B7 cells, which are LLCPK cells stably transfected with the human PTH1R, were kindly provided by Tom Gardella, Endocrine Unit, Massachusetts General Hospital. The cells are described in reference (7). HKrK-B7 cells were grown in 24 well plates to 90 percent confluence, which was typically achieved 2-3 days after initial seeding. The culture media was DMEM (with L-glutamine)+10% fetal bovine serum (FBS).

When the cells reached 90% confluence, the cells were rinsed once with 0.5 ml binding buffer (50 mM Tris-HCl, pH 7.8, 100 mM NaCl, 2 mM $CaCl_2$, 5 mM KCl, 0.25% horse serum, 0.0025% fetal bovine serum). The plate was placed on ice, and 200 microliters IBMX buffer (DMEM without antibiotic and FBS, 35 mM HEPES, pH 7.4, 3-isobutyl-1-methylxanthine (IBMX), 1 mg/ml bovine serum albumin) was added per well. IBMX is a phosphodiesterase inhibitor. Peptide or PTH was added at the indicated concentrations in 100 microliters binding buffer. The cells were then incubated with the peptide, PTH, or no addition (control) for 1 hour at room temperature. The media was then removed and the plates were placed on dry ice to freeze the cells for 3 minutes. 500 microliters 50 mM HCl was next added to each well. The plates were kept frozen until the immunoassay.

cAMP concentration was measured by immunoassay (Biomedical Technologies, Inc., Stoughton, Mass., USA; cAMP EIA kit, #BT-730).

Figure 2:
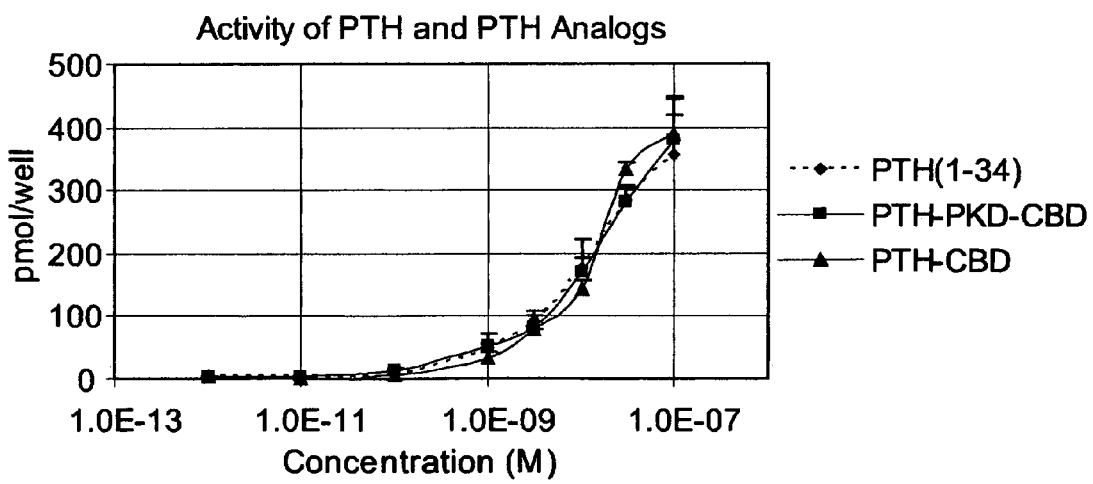
FIG. 2 is a graph showing in vitro cAMP accumulation in cells stimulated with PTH(1-34) or PTH-CBD fusion proteins.

The results of the cAMP concentration from the lysed cells in the wells is shown in FIG. 2 for cells incubated with from $1 \times 10^{-12}$ M to $1 \times 10^{-7}$ M fusion peptide or PTH(1-34). PTH (1-34), PTH-CBD (SEQ ID NO:1), and PTH-PKD-CBD (SEQ ID NO:2) all stimulated cAMP synthesis to a similar extent.

Example 4

In Vivo Activity of PTH-CBD Fusion Proteins

Healthy female C57BL/6J mice, 5-8 weeks age and 13-18 grams, were purchased from the Jackson laboratory (Bar Harbor, Me., USA) and they were housed in cages at the Animal facility in Ochsner Clinic Foundation under standard conditions. Animals were maintained for a 2-week acclimation period prior to experiments.

Baseline whole body DEXA (dual emission x-ray absorptiometry) measurements were obtained in duplicate for each animal using a Hologic QDR-1000 plus instrument adapted for application in the mouse as follows. An ultrahigh resolution mode (line spacing 0.03950 cm and resolution 0.03749 cm) was used. The animals were anesthetized with pentobarbital and positioned in the prone position for DEXA scanning. Bone mineral density (BMD) was determined within an 8×16 pixel box covering the region of the lumbar spine. BMD for each single pixel vertical stripe was measured, and the peak values were determined. Validity for this technique was ascertained by comparing the duplicate measurements in each mouse.

Animals were injected intraperitoneally weekly for eight weeks with either vehicle alone (collagen binding buffer, pH 7.5, 50 mM Tris HCl, 5 mM $CaCl_2$) or vehicle containing PTH analogs as follows:

Group A (8 animals): vehicle
Group B (6 animals): 80 µg/kg/dose of human PTH(1-34)
Group C (6 animals): 546 µg/kg/dose of PTH-PKD-CBD (SEQ ID NO:2)
Group D (6 animals): 344 µg/kg/dose of PTH-CBD (SEQ ID NO:1)

The doses of the three PTH compounds were adjusted based on their molecular weights, such that each was given at the same molar equivalent (0.02 micromoles/kg/dose).

Figure 3:
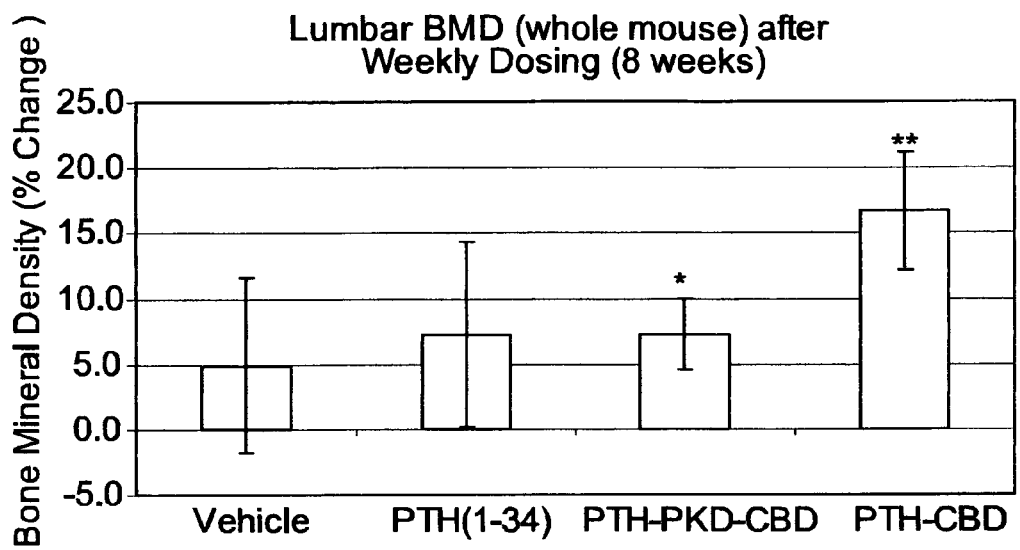
FIG. 3 is a bar graph showing increase in spinal bone mineral density in mice treated with weekly intraperitoneal injection for 8 weeks of buffer (vehicle), PTH(1-34), PTH-PKD-CBD fusion protein, or PTH-CBD fusion protein.

One week after the 8th injection, animals were sacrificed with a lethal dose of pentobarbital. Duplicate BMD measurements were obtained for each mouse by the technique described above. Percent increase in BMD for each mouse was calculated, and the results (average+/−standard error) are shown in FIG. 3. Statistical significance was determined using a one-tailed paired T test. Statistically significant differences from vehicle control are shown by * ($p<0.05$) and ** ($p<0.01$) in FIGS. 3 and 4.

At the conclusion of the study, lumbar spine segments of the mice were also excised from the soft tissue and BMD measurements of the excised spine segments were taken. The BMD results of the excised spine segments are the average for the entire bone segment, not peak BMD measurements like those that were obtained from the whole animal scans.

The statistical comparisons used were ANOVA across groups (p<0.05), and Bonferroni comparisons of each group vs. control.

The PTH-CBD fusion protein (SEQ ID NO:1) produced an average 17% increase in BMD over the 8-week treatment period. Both PTH(1-34) and the PTH-PKD-CBD fusion protein (SEQ ID NO:2) produced approximately a 7.5% increase in bone mineral density. The mice in the vehicle control group had a 5% increase in BMD over the 8-week treatment period. (FIG. 3.) Both PTH-CBD (p<0.01) and PTH-PKD-CBD (p<0.05) fusion proteins produced BMD increases that were statistically significantly greater than vehicle controls, while PTH(1-34) did not. But the PTH-CBD fusion gave approximately twice the BMD increase of both PTH(1-34) and the PTH-PKD-CBD fusion protein. (FIG. 3)

Figure 4:
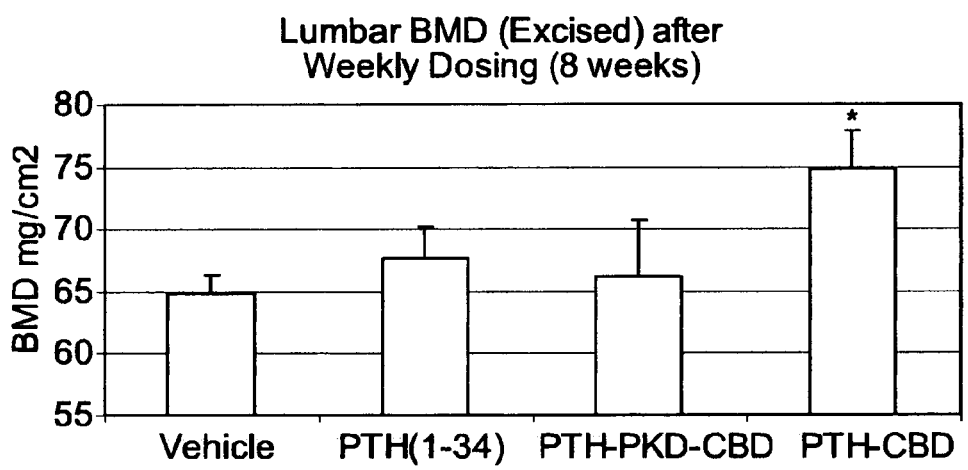
FIG. 4 is a bar graph showing absolute spinal bone mineral density of excised spine segments from mice sacrificed after treatment for 8 weeks with weekly intraperitoneal injection of buffer (vehicle), PTH(1-34), PTH-PKD-CBD fusion protein, or PTH-CBD fusion protein.

The BMD of excised lumbar spine segments of the four groups of mice at the conclusion of the 8-week treatment period are shown in FIG. 4. Again, the PTH-CBD group was statistically significantly different from the vehicle control (p<0.05). Differences between other groups with vehicle control and with each other did not reach statistical significance.

Figure 5:
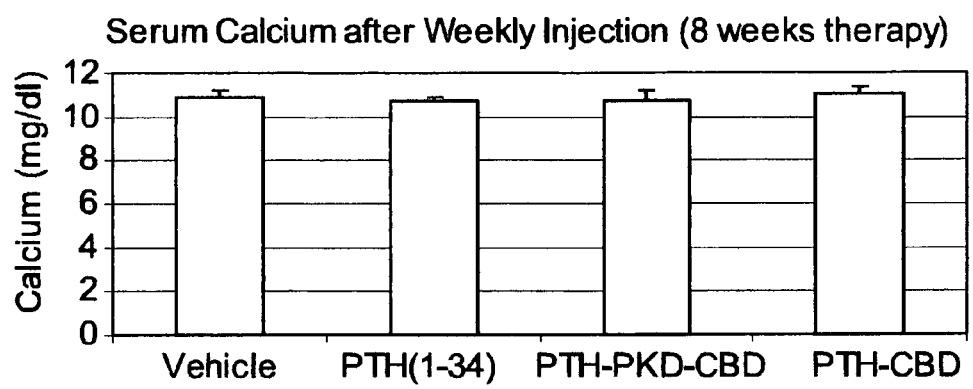
FIG. 5 is a bar graph showing serum calcium levels of mice after 8 weeks of weekly injections of buffer (vehicle), PTH (1-34), PTH-PKD-CBD fusion protein, or PTH-CBD fusion protein.

Serum calcium levels were also measured in the mice before, during, and after the study. PTH with daily injection is known to carry a risk of hypercalcemia. There was no difference in serum calcium levels between any of the groups, indicating that the PTH-CBD fusion proteins did not cause hypercalcemia (FIG. 5).

Figure 6:
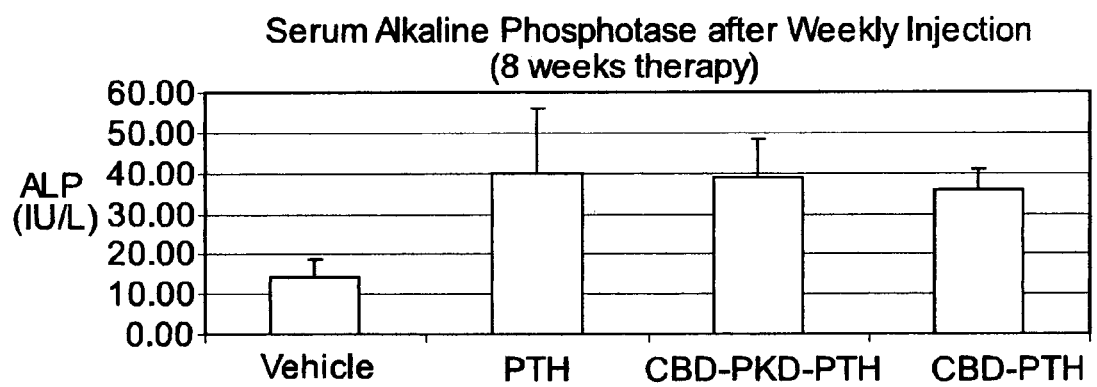
FIG. 6 is a bar graph showing serum alkaline phosphatase concentration of mice after 8 weeks of weekly injections of buffer (vehicle), PTH(1-34), PTH-PKD-CBD fusion protein, or PTH-CBD fusion protein.

Serum alkaline phosphatase levels were also measured. Serum alkaline phosphatase was increased in the PTH(1-34), PTH-PKD-CBD, and PTH-CBD groups (FIG. 6). Elevated alkaline phosphatase is correlated with hyperparathyroidism and periods of bone growth. Thus, this is evidence of increased bone turnover with all three agents.

Figure 7:
FIG. 7 is a micrograph of sections of tibia bone from a vehicle-treated control mouse and a mouse receiving 8 weeks of weekly injection of PTH-CBD fusion protein. The sections were stained with hematoxylin and eosin stain. The micrograph shows increased cortical and trabecular bone mass in the bone of the mouse treated with PTH-CBD.

Staining of tibial sections with hematoxylin and eosin showed increased trabecular and cortical bone in mice treated with 8 weeks of PTH-CBD versus vehicle control (FIG. 7).

No evidence of bone tumors in mice in any of the groups was found by DEXA or post-mortem examination.

We conclude that the PTH-CBD fusion protein is more active than PTH(1-34) in promoting bone mineral density increase in vivo.

Example 5

Monthly Administration of PTH-CBD In Vivo

With the encouraging results showing efficacy of PTH-CBD to increase bone mineral density after weekly administration, we next tested the efficacy of this fusion protein with monthly administration. Mice received intraperitoneal injection of PTH-CBD (344 μg/kg/dose), PTH (80 μg/kg/dose), or vehicle alone monthly in buffer as described in Example 4. There were 10 mice in each group. Bone mineral density (BMD) was measured by DEXA as described in Example 4 every 2 months. DEXA measurements were correlated to absolute bone mineral density by correlation between DEXA measurements and measurements from excised tissue in the weekly study of Example 4.

Figure 8:
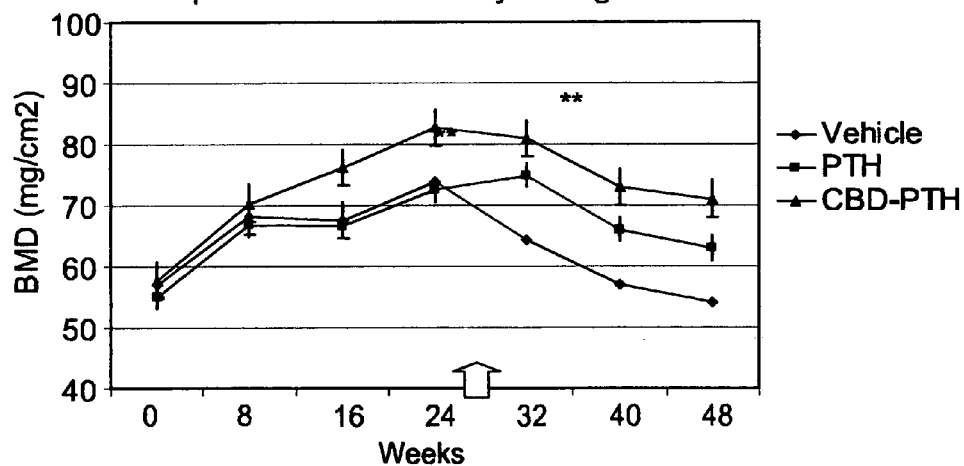
FIG. 8 is line graph of bone mineral density over time for mice treated monthly with PTH-CBD, PTH(1-34), or vehicle control for 6 months. At 6 months, the group receiving PTH (1-34) was treated daily for two weeks (indicated by the arrow on the X axis). Then all groups were untreated for the rest of the study.

Serial measurements of BMD every 2 months showed that monthly administration of PTH-CBD resulted in significant increases in BMD after 4 months of therapy, which were sustained for 6 months of therapy (FIG. 8) (p<0.01, shown by ** in FIG. 8). Not surprisingly, monthly administration of PTH(1-34) had no effect on bone mineral density. After 6 months (as indicated by the arrow in FIG. 8), we discontinued administration of PTH-CBD, and subjected the animals in the PTH(1-34) group to 2 weeks of daily therapy. Measurement of BMD 2 months later showed that the gains in bone mineral density after PTH-CBD administration were sustained (despite the decline in BMD in the vehicle control group, expected for age), and that the daily administration of PTH (1-34) resulted in increases in BMD which approached but did not reach those of the PTH-CBD group.

The mice were then followed for another 6 months, and the data showed that the BMD of the PTH(1-34) and PTH-CBD groups declined in parallel and remained higher than the untreated vehicle control mice.

Figure 10:
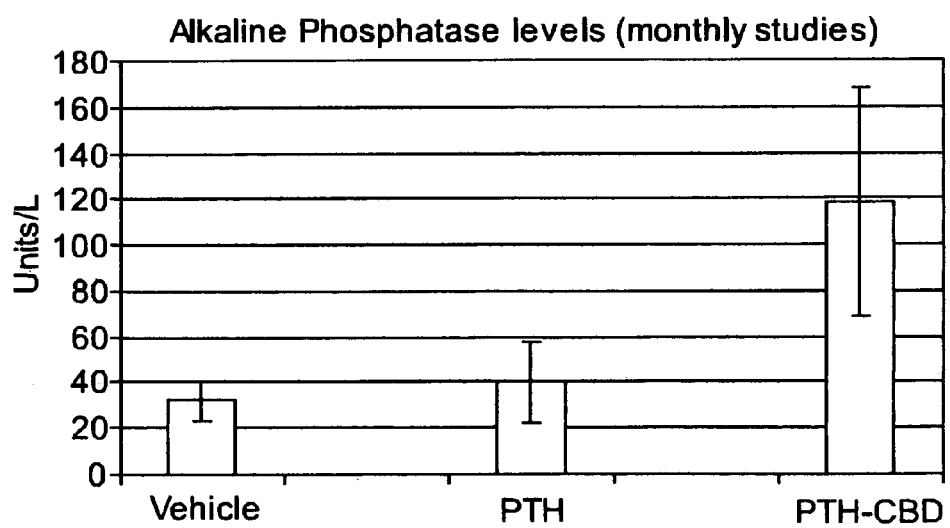
FIG. 10 is a bar graph showing serum alkaline phosphatase concentration of mice after 8 weeks of weekly injections of buffer (vehicle), PTH(1-34), PTH-PKD-CBD fusion protein, or PTH-CBD fusion protein.

Serum concentration of alkalaline phosphatase was also measured in these groups of mice at the 48-week time point. The results are shown in FIG. 10. Even at 48 weeks, 22 weeks after the last administration of the PTH-CBD fusion protein, alkaline phosphatase concentration was elevated in the group receiving the PTH-CBD fusion protein compared to the vehicle control mice and mice that received PTH(1-34).

Conclusion:

Together with the data in Example 4, these data indicate that monthly administration of PTH-CBD showed at least equal efficacy to daily injection of PTH in promoting an increase in bone mineral density. Importantly, the dose of PTH-CBD given in each injection is the molar equivalent of the daily dose of PTH(1-34); thus, the total administered dose is actually 1/30 of the dose with PTH(1-34). The data suggests that even longer dosing intervals than monthly may be effective, and that the effects on BMD are sustained for a longer time after cessation of therapy with PTH-CBD than with PTH(1-34).

Example 6

3- and 6-Monthly Administration of PTH-CBD In Vivo

Figure 9:
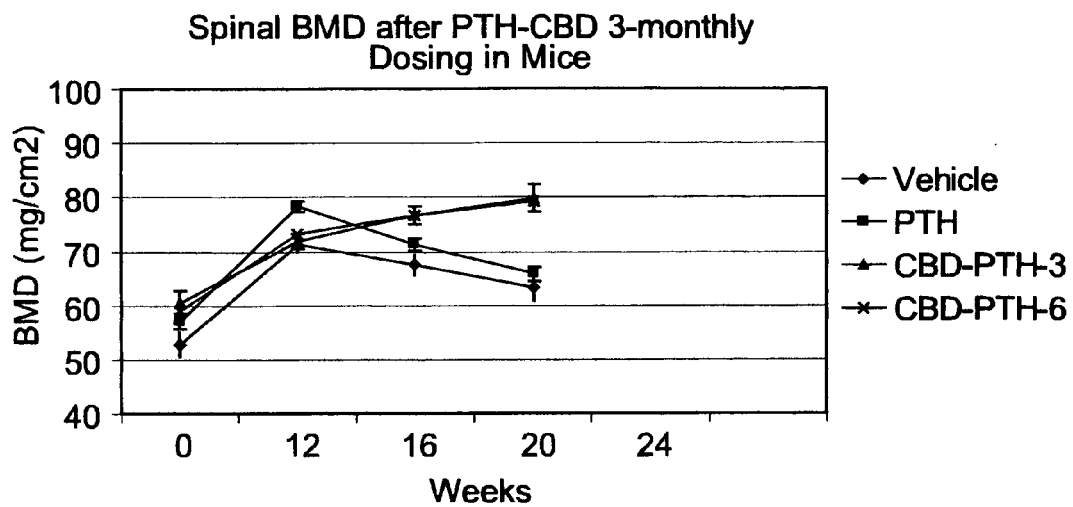
FIG. 9 is a line graph of bone mineral density over time for mice treated with PTH(1-34) daily for 14 days (PTH), with the PTH-CBD fusion protein once at the initiation of the study (CBD-PTH-6), with PTH-CBD fusion protein at time 0 and a second time at 3 months (CBD-PTH-3), and with vehicle control.

With the encouraging results showing efficacy of PTH-CBD to increase bone mineral density after monthly administration, we next tested the efficacy of this fusion protein with administration every 3 or every 6 months. Mice received intraperitoneal injection of PTH-CBD (344 μg/kg/dose×1) (CBD-PTH-6 of FIG. 9), PTH-CBD (344 μg/kg/dose at 0 and 3 months) (CBD-PTH-6 of FIG. 9), PTH(1-34) (80 μg/kg/dose daily for 2 weeks), or vehicle alone (×1) in buffer as described in Example 4. There were eleven mice in each group. Bone mineral density (BMD) was measured by DEXA at 3 month and monthly thereafter. The study is ongoing, and data are available up to the 5 month time point Serial measurements of BMD showed that a single dose of PTH-CBD resulted in significant increases in BMD after 4 months of therapy (FIG. 9). Administration of the second dose of PTH-CBD at the 3 month time point did not cause further increases in BMD at the 4 and 5 month time points. Daily administration of PTH(1-34) for 2 weeks caused the expected increase in BMD at 3 months, but by 5 months the BMD had declined back to control levels. The mice in this study will be followed for an additional 7 months.

Conclusion:

Together with the data in Examples 4 and 5, these data suggest that a single dose of PTH-CBD is sufficient to promote sustained increases in bone mineral density. Importantly, the dose of PTH-CBD given in each injection is the molar equivalent of the daily dose of PTH(1-34); thus, the total administered dose is actually 1/14 of the dose of PTH(1-34) over the 5 month interval for which we have data at this time. We will continue to collect data on this study for another 7 months. The data also indicate that the effects on BMD are sustained for a longer time after cessation of therapy with PTH-CBD than with PTH(1-34).

Example 7

Preliminary Dose and Time Response Study

Figure 11:
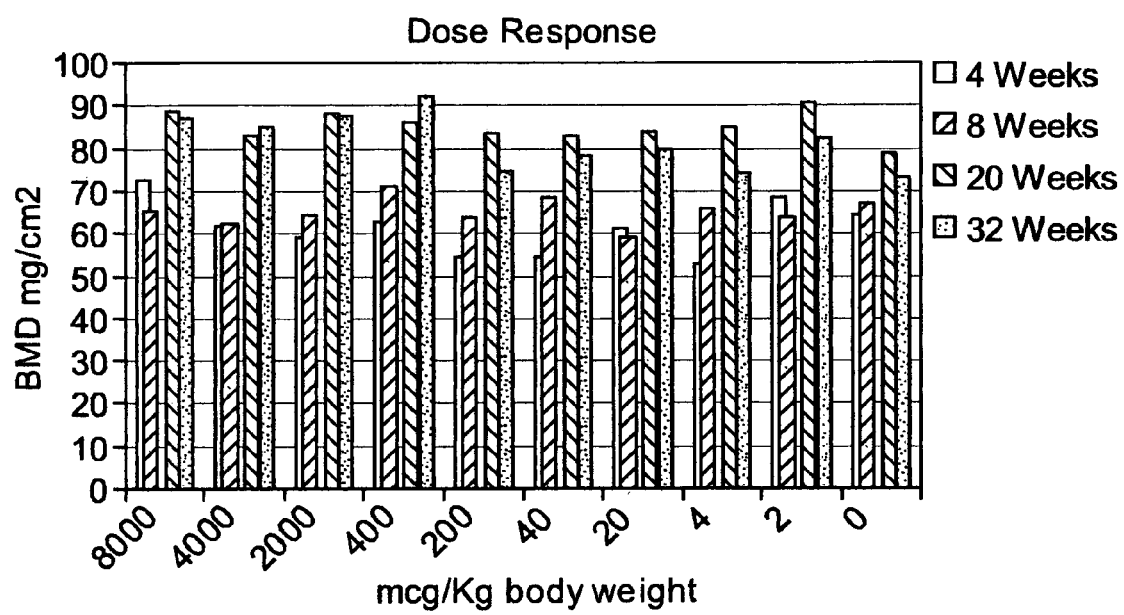
FIG. 11 is a bar graph of bone mineral density in mice receiving a single dose of a range of dosage amounts of PTH-CBD by subcutaneous injection. Bone mineral density was followed for 32 weeks. Each dosage was given to two mice.

To determine roughly the optimal dose of PTH-CBD, a single dose of the fusion protein was given by subcutaneous administration to mice at a range of doses from 2 to 8,000 micrograms/kg and the BMD of the mice was tested by DEXA every 4 weeks for 20 weeks. At the highest dose, the BMD decreased between 4 weeks and 12 weeks and then increased. It thus appeared to have a transient catabolic effect and then a possible anabolic effect. Intermediate doses of 40-400 micrograms/kg, which spans the dose of 344 micrograms/kg used in Example 4 and 5, appeared to have the greatest anabolic effect over the first 8 weeks. The lowest dose tested, 2 micrograms/kg appeared to have less anabolic effect over the first 16 weeks. (FIG. 11)

Example 8

Use of PTH-CBD to Promote Hair Growth

There are reports that PTH agonists and antagonists can modulate hair growth in animal models of genetic hair loss and after administration of chemotherapy (8,9). We tested whether PTH-CBD could, after subcutaneous administration, alter the pattern of hair growth after chemotherapy-induced hair loss with cyclophosphamide.

Materials and Methods:

Healthy female C57BL/6J mice (as in Example 4) were treated with 150 mg/kg cyclophosphamide every month for 3 months. The chemotherapeutic agent caused hair thinning and color change from black to white. We additionally shaved a spot on the back. At the spot of hair removal, we injected PTH-CBD subcutaneously at a dose of 320 mg/kg. We also tested injection of a CBD fusion protein containing a PTH/PTHrP receptor antagonist (SEQ ID NO:9). This fusion protein was made by inserting a thrombin cleavage sequence (Leu-Val-Pro-Arg-Gly-Ser, SEQ ID NO:12) between the GST and PTH(1-33) segments of the fusion protein of SEQ ID NO:1. The resultant GST-PTH-CBD fusion protein is cleaved by thrombin between the Arg and Gly residues of the thrombin cleavage sequence to release the Gly-Ser-PTH-CBD fusion protein of SEQ ID NO:9.

Figure 12:
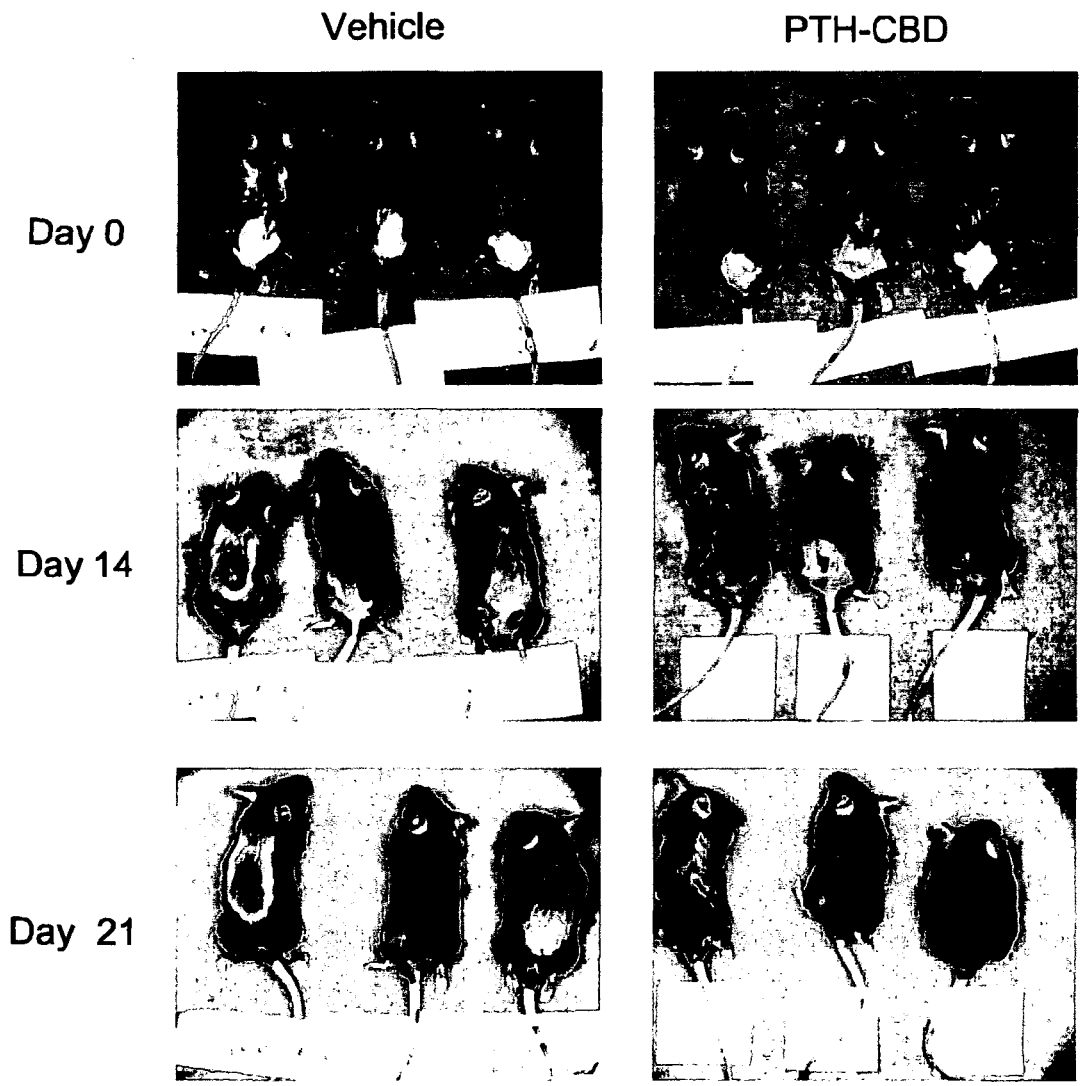
FIG. 12 shows photographs of mice described in Example 8 having chemotherapy-induce alopecia and a shaved spot on their backs, treated with the PTH-CBD fusion protein by subcutaneous injection at the hairless spot, or untreated controls. There are 3 mice in each group, and photos are taken at 0 days, 14 days, and 21 days after the injection of PTH-CBD. The photos show greater hair growth in the subjects treated with the PTH-CBD fusion protein.

Results:

The PTH-CBD treated animals showed more rapid regrowth of hair at the spot of removal, and the chemotherapy-induced thinning and color change of the hair were both reversed, even at sites distant from the PTH-CBD injection site (FIG. 12). A CBD fusion protein containing a PTH/PTHrP receptor antagonist was also tested in pilot studies. But the antagonist fusion protein produced only peach fuzz hair at the site of injection and did not work as well as the PTH-CBD agonist fusion protein (results not shown). The antagonist fusion protein produced more hair than vehicle control treatment (results not shown).

Conclusion:

PTH-CBD can reverse chemotherapy-induced alopecia, and the effects are not restricted to the site of injection.

Example 9

Use of PTH-CBD to Promote Immune Reconstitution

Female C57Bl/6 mice are irradiated with 10 Gy of radiation ($^{137}$Cs source). 24 hours later, mice are injected with $2 \times 10^5$ bone marrow mononuclear cells (BMMNC) from a donor B6.SJL mouse. Immediately before receiving the BMMNC, the recipient mice are also injected with saline (vehicle control), 344: g/kg PTH-CBD (SEQ ID NO:1), or 80: g/kg PTH(1-34).

A portion or all of the mice receiving BMMNC alone are expected to die. A greater percentage of mice receiving PTH (1-34) are expected to survive. A still greater percentage of mice receiving PTH-CBD are expected to survive.

It is also expected that neutrophil count will increase faster in mice receiving the PTH-CBD fusion than in mice receiving an equimolar amount of PTH or receiving vehicle control.

Example 10

Use of PTH-CBD to Promote Bone Marrow Stem Cell Mobilization

Six- to 8-week old male C57BL/6 mice are injected subcutaneously with a single dose of 80 mcg/kg PTH(1-34) or 344 mcg/kg PTH-CBD (SEQ ID NO:1) or saline (vehicle control). Fourteen days later, peripheral blood is collected from the mice, and c-KIT/Sca-1 cells are determined by fluorescence activated cell sorting (FACS) (21). It is determined that PTH-CBD causes a greater increase in c-KIT/Sca-1 double positive cells than a single dose of PTH(1-34).

To test the ability of stem cells mobilized with PTH-CBD to repopulate, blood is collected 14 days after treatment with PTH, PTH-CBD, or vehicle control as described above. Red cells are lysed as described in (22). Total collected cells from 900 mcl of blood is transfused into a mouse that was subjected to a lethal dose of radiation (900 cGy) 24 hours before. A larger percentage of recipient mice are expected to survive when given blood cells from a donor mouse treated with PTH-CBD than from a mouse treated with PTH(1-34) or vehicle control. Further, it is expected that administering the fusion protein will increase the number of stem cells in circulating blood of the mammal (e.g., 7, 14, or 30 days after administering the fusion protein)

Example 11

Use of a CBD-PTH/PTHrP Receptor Antagonist Fusion Protein for the Prevention and Treatment of Bone Metastasis of Breast Cancer When administered as a daily injection, PTH(1-34) stimulates bone growth in various species and in osteoporotic women. However, continuous administration of PTH as an infusion (i.e. parathyroid adenoma) results in bone loss.

Breast cancer metastasizes to bone by producing a factor, PTH-related peptide (PTHrP), which activates the PTH/PTHrP receptor, increasing bone turnover in the local region. The removal of bone tissues which results from this cascade creates a void in the bone where cancer cells can grow and causes release of growth factors from the remodeled collagen matrix which promote tumor growth. In this study, we show that a PTH-CBD antagonist peptide has the ability to treat or prevent (reduce incidence of) bone metastasis of breast cancer. The model used is the immunodeficient nude mouse.

Animals receive a single injection of MCF-7 human breast cancer cells tagged with a phosphorescent probe. Animals are imaged weekly using a whole body imager to assess for bone metastatic lesions. Once 2 or more lesion are present in each animal, the animals receive a single injection of PTH(7-33)-CBD or vehicle control. Weekly imaging is continued for an additional 2 months to monitor growth of existing metastases and appearance of new metastases.

Experimental Methods:

22 Nude mice, aged 3-5 weeks and 13-18 grams are obtained. Initial weight of the animals is recorded along with their general health condition. Animals are maintained for a 2 week acclimation period prior to experiments. (final age 5-8 weeks).

Baseline images are obtained from each animal using the Bioluminescent/Fluorescent Imager (Xenogen Biosciences, Cranbury, N.J.) whole body imager after isoflourane anesthesia. Animals then receive a single injection of MCF-7 cells stably transfected with a plasmid expressing firefly luciferase (23, 24). Animals are re-imaged following the injection and on a weekly basis thereafter to monitor for bone metastasis.

When 2 or more metastatic lesions are presenting the bones of each mouse, the animals will be divided randomly into 2 groups:

Group 1: 11 animals—is administered with vehicle intraperitoneally once.
Group 2: 11 animals—is administered with 344 mcg/kg of PTH(7-33)-CBD (SEQ ID NO:10) intraperitoneally once.

Animals are sedated with isoflourane and whole body images are obtained on a weekly basis for a 2 month period.

Data Analysis:

During the experimental period, animals are weighed and examined weekly to detect any signs of illness. Whole body images are analyzed to determine the number of metastatic lesions and intensity of the luminescent light emmission from each lesion.

At the end of the experimental period the animals will be sacrificed by injecting a lethal dose of pentobarbital (100 mg/kg). Regions of the bone which contain(ed) metastatic lesions at any point during the study are prepared for histological examination.

Results:

Mice injected with PTH(7-33)-CBD are expected to develop fewer metastatic bone lesions and have slower growth of metastatic bone lesions than mice receiving vehicle control.

Example 12

Use of a CBD-PTH/PTHrP Receptor Antagonist Fusion Protein for the Prevention and Treatment of Renal Osteodystrophy Renal osteodystrophy is a bone disease that occurs when kidneys fail to maintain the proper levels of calcium and phosphorus in the blood. It's a common problem in people with kidney disease and affects 90 percent of dialysis patients. Renal osteodystrophy is a key cause of fractures in patients with chronic kidney disease. In this study, we show that PTH-CBD antagonist peptide has the ability to treat or prevent osteodystrophy. The model used is normal female mice fed with a high phosphorus diet to induce renal osteodystrophy.

Animals then receive a single injection of PTH(7-33)-CBD or vehicle control. Animals are maintained for 6 months after the initial dosing period to assess the duration of the therapeutic effects. Bone mineral density and alkaline phosphatase levels are measured on a monthly basis.

Experimental Plan:

Healthy female normal C57BL/6J mouse, aged 3-5 weeks and 13-18 grams are obtained. Initial weight of the animals is recorded along with their general health condition. Animals are maintained for a 2 week acclimation period prior to experiments (final age 5-8 weeks).

Animals are fed with high phosphorus diet to induce renal osteodystrophy (ROD). The animals are checked periodically for their health status. The blood samples are collected to assess the calcium, phosphorus, PTH and Vitamin D levels. Renal osteodystrophy results from an abnormally elevated serum phosphate (hyperphosphatemia) and low serum calcium (hypocalcemia), both of which are due to decreased excretion of phosphate by the damaged kidney, low vitamin D levels or tertiary hyperparathyroidism (dysfunction of the parathyroid gland due to constant stimulation).

Baseline bone mineral density measurements are also be made.

The animals are divided into the following groups:

Group 1: 11 animals—are administered vehicle intraperitoneally once.
Group 2: 11 animals—are administered with 344 mcg/kg of PTH(7-33)-CBD (SEQ ID NO:10) intraperitoneally once.

Animals are sedated with pentobarbital and bone mineral density (BMD) is measured at the start of the study and monthly for the duration of the study (6 months). Blood samples are obtained from tail clipping at the start of the study and every month (under sedation as above).

Data Analysis:

During the experimental period, animals are weighed and examined weekly to detect any signs of illness. Bone mineral density measurements are analyzed by ANOVA at each time point. Alkaline phosphatase and calcium values are measured from each blood sample and analyzed by ANOVA at each time point.

At the end of the experimental period the animals are sacrificed by injecting a lethal dose of pentobarbital (100 mg/kg). Blood samples are collected to perform biochemical assays (intact PTH, calcium, phosphorus, alkaline phosphatase, osteocalcin). Quantitative bone assays include histomorphometry, BMC and BMD of the total body and excised spine, and assessment of biomechanical properties. Data is analyzed by ANOVA.

Results:

The animals injected with PTH(7-33)-CBD are expected to respond with increases or slower decreases in all measures of bone mineral density as compared to mice receiving vehicle control. Mice injected with PTH(7-33)-CBD are expected also to show trabecular bone growth or slower loss of trabecular bone than mice receiving vehicle control.

Sequence Listing Summary

SEQ ID NO:1 PTH-CBD fusion protein
SEQ ID NO:2 PTH-PKD-CBD fusion protein
SEQ ID NO:3 vector expressing PTH-CBD fusion protein precursor.
SEQ ID NO:4 GST-PTH-CBD fusion protein expressed by vector.
SEQ ID NO:5 Factor Xa recognition sequence.
SEQ ID NO:6 ColH collagenase.
SEQ ID NO:7 PTH.
SEQ ID NO:8 PTHrP.
SEQ ID NO:9 CBD fusion protein with PTH receptor antagonist.
SEQ ID NO:10 PTH(7-33)-CBD fusion protein
SEQ ID NO:11 PTH/PTHrP antagonist Gly-Ser-PTH(1-33)
SEQ ID NO:12 Thrombin recognition sequence.

REFERENCES

1. Broadus A E et al. 1988. *N. Engl. J. Med.* 319:556-563.
2. Thiede M A et al. 1988. *Proc. Natl. Acad. Sci. USA* 85:4605-4609.
3. Orloff, J J et al. 1994. *Endocrine Rev.* 15:40-60.
4. Schilli, M B et al. 1997. *J. Invest. Dermatol.* 108:928-932.
5. Matsushita, O. et al. 1999. *J. Bacteriol.* 181:923-933.
6. Yoshihara, K. et al. 1994. *J. Bacteriol.* 176:6489-6496.
7. Jonsson K B, John M R, Gensure R C, Gardella T J, Juppner H. 2001. Tuberoinfundibular peptide 39 binds to the parathyroid hormone (PTH)/PTH-related peptide receptor, but functions as an antagonist. *Endocrinology* 142(2):704-9.
8. Schilli M B, Ray S, Paus R, Obit-Tabot E, Holick M F. 1997. Control of hair growth with parthyroid hormone (7-34). *J. Invest. Dermatol.* 108:928-932.
9. Peters E M, Foitzik K, Paus R, Ray S, Holick M F. 2001. A new strategy for modulating chemotherapy-induced alopecia, using PTH/PTHrP receptor agonist and antagonist. *J Invest Dermatol.* 117(2):173-8.
10. Ballen K. 2007. Targeting the stem cell niche: squeezing blood from bones. *Bone Marrow Transplantation* 39:655-660.
11. Ballen K. et al. 2007. Phase I trial of parathyroid hormone to facilitate stem cell mobilization. *Biology of Blood and Marrow Transplantation* 13:838-843.
12. Calvi L M et al. 2003. Osteoblastic cells regulate the haematopoietic stem cell niche. *Nature* 425:841-846.
13. Wuthrich R P, Martin D, Bilezikian J P. 2007. The role of calcimimetics in treatment of hyperparathyroidism. *Eur. J. Clin. Invest.* 37:915-922.
14. Dolgos S. et al. 2008. Determinants of bone mass in end-stage renal failure patients at the time of kidney transplantation. *Clin. Transplant.* epub ahead of print.
15. Guise T A. 1997. Parathyroid hormone-related protein and bone metastases. *Cancer* 80(8 Suppl): 1572-80.
16. Henderson M A, Danks J A et al. 2006. Parathyroid hormone-related protein localization in breast cancers predicts improved prognosis. *Cancer Res.* 66:2250-56.
17. Saito H, Tsunenari T et al. 2005. Humanized monoclonal antibody against parathyroid hormone-related protein suppresses osteolytic bone metastasis of human breast cancer cells derived from MDA-MB-231. *Anticancer Res.* 25:3817-23. Erratum in 26:445.
18. Hoare S R, Usdin T B. 2002. Specificity and stability of a new PTH1 receptor antagonist, mouse TIP(7-39). *Peptides* 23:989-98.
19. Rickard D J et al. 2007. Intermittent treatment with parathyroid hormone as well as a non-peptide small molecule agonist of the PTH1 receptor inhibits adipocyte differentiation in human bone marrow stromal cells. *Bone* 39:1361-1372.
20. McDonald I M et al. 2007. Discovery and characterization of novel, potent, non-peptide parathyroid hormone receptor antagonists. *J. Med. Chem.* 50:4789-4792.
21. Stokman G et al. 2008. Enhanced mobilization of bone marrow cells does not ameliorate renal fibrosis. *Nephrol. Dial. Transplant* 23:483-491.
22. Abraham M et al. 2007. Enhanced unique pattern of hematopoietic cell mobilization induced by the CXCR4 antagonist 4F-benzoyl-TN14003. *Stem cells* 25:2158-2166.
23. Caceres G et al. 2003. Determination of chemotherapeutic activity in vivo by luminescent imaging of luciferase-transfected human tumors. *Anticancer Drugs* 14:569-74.
24. Jenkins D E et al. 2005. Bioluminescent human breast cancer cell lines that permit rapid and sensitive in vivo detection of mammary tumors and multiple metastases in immune deficient mice. *Breast Cancer Research* 7:R444-R454.
25. Compston J E. 2007. Skeletal actions of intermittent parathyroid hormone: effects on bone remodelling and structure. *Bone* 40(6):1447-52.
26. Fox J, Miller M A, Newman M K, Recker R R, Turner C H, Smith S Y. 2007. Effects of daily treatment with parathyroid hormone 1-84 for 16 months on density, architecture and biomechanical properties of cortical bone in adult ovariectomized rhesus monkeys. *Bone* 41(3):321-30.
27. Zhou H, Iida-Klein A, Lu S S, Ducayen-Knowles M, Levine L R, Dempster D W, Lindsay R. 2003. Anabolic action of parathyroid hormone on cortical and cancellous bone differs between axial and appendicular skeletal sites in mice. *Bone* 32(5):513-20.
28. Zaruba M M, Huber B C, Brunner S, Deindl E, David R, Fischer R, Assmann G, Herbach N, Grundmann S, Wanke R, Mueller-Hoecker J, Franz W M. 2008. Parathyroid hormone treatment after myocardial infarction promotes cardiac repair by enhanced neovascularization and cell survival. *Cardiovasc Res.* 77(4):722-31.
29. Schlüter K D, Schreckenberg R, Wenzel S. 2008. Stem cell mobilization versus stem cell homing: potential role for parathyroid hormone? *Cardiovasc Res.* 77(4):612-3.
30. Ishikawa et al., U.S. published patent application 20040053368.
31. Goldberg et al., International patent application WO 2005/082941.
32. Ishikawa T, Eguchi M, Wada M, Iwami Y, Tono K, Iwaguro H, Masuda H, Tamaki T, Asahara T. 2006. Establishment of a Functionally Active Collagen-Binding Vascular Endothelial Growth Factor Fusion Protein In Situ. *Arterioscler Thromb Vasc Biol.*
33. Ishikawa T, Terai H, Yamamoto T, Harada K, Kitajima T. 2003. Delivery of a growth factor fusion protein having collagen-binding activity to wound tissues. *Artif Organs.* 27(2): 147-54.
34. Crine et al., U.S. published patent application 20060014687.

All patents, patent documents, and other references cited are incorporated by reference.

We claim:

1. A composition comprising:
a collagen-binding polypeptide segment covalently linked to a PTH/PTHrP receptor agonist; wherein the collagen-binding polypeptide segment is a bacterial collagen binding polypeptide segment, wherein the PTH/PTHrP receptor agonist comprises residues 1-14 of SEQ ID NO: 1, and wherein the collagen-binding polypeptide segment comprises residues 38-158 of SEQ ID NO: 1, or is at least 90% identical to residues 38-158 of SEQ ID NO: 1.

2. The composition of claim 1, wherein the collagen-binding polypeptide segment and the PTH/PTHrP receptor agonist are chemically cross-linked to each other or are polypeptide portions of a fusion protein.

3. The composition of claim 1, wherein the N-terminus of the collagen-binding polypeptide segment is linked directly or through a linker polypeptide segment to the C-terminus of the PTH/PTHrP receptor agonist polypeptide.

4. The composition of claim 1, wherein the composition comprises SEQ ID NO: 1.

5. The composition of claim 1, wherein the composition comprises SEQ ID NO: 2.

6. The composition of claim 1, wherein the PTH/PTHrP receptor agonist comprises residues 1-33 of SEQ ID NO: 1.

7. The composition of claim 1, wherein the composition further comprises residues 37-251 of SEQ ID NO: 2 covalently linked to collagen binding polypeptide segment.

* * * * *